(12) United States Patent
Miller et al.

(10) Patent No.: US 8,784,899 B2
(45) Date of Patent: Jul. 22, 2014

(54) COMPOSITIONS AND METHODS FOR CANCER TREATMENT

(75) Inventors: Wilson H. Miller, Montreal (CA); Zuanel Diaz Heredia, Montreal (CA); Hyman M. Schipper, Montreal (CA); Koren K. Mann, Montreal (CA)

(73) Assignee: Samuel Waxman Cancer Research Foundation, New York, NY (US)

( * ) Notice: Subject to any disclaimer, the term of this patent is extended or adjusted under 35 U.S.C. 154(b) by 1214 days.

(21) Appl. No.: 11/542,645

(22) Filed: Oct. 4, 2006

(65) Prior Publication Data

US 2007/0104800 A1   May 10, 2007

Related U.S. Application Data

(60) Provisional application No. 60/722,970, filed on Oct. 4, 2005.

(51) Int. Cl.
*A61K 31/355*   (2006.01)
*A61K 33/36*   (2006.01)

(52) U.S. Cl.
CPC .............. *A61K 33/36* (2013.01); *A61K 31/355* (2013.01)
USPC .......................................... 424/623; 514/458

(58) Field of Classification Search
USPC .......................................... 424/623; 514/458
See application file for complete search history.

(56) References Cited

U.S. PATENT DOCUMENTS 5,478,812 A *  12/1995  Murase et al. ................. 514/32
5,498,427 A *   3/1996  Menasche .................... 424/678
6,875,451 B2 *  4/2005  Ellison et al. ................. 424/623

OTHER PUBLICATIONS

Diaz et al., Blood, 105:1237-1245 (2005; prepublished online Oct. 5, 2004).*
Soignet et al., The New England Journal of Medicine, 339(10), 1341-1348 (1998).*
Gerhauser et al., Mutation Research 523-524 (2003) 163-172.*
Chinery et al, "Antioxidants enhance the cytotoxicity of chemotherapeutic agents in colorectal cancer: A p53-independent induction of p21(WAF1/CIP1) via C/EBPB", Nature Medicine, 3(11), pp. 1233-2141 (1997).*
Verma et al, "Arsenic toxicity in mice and its possible amelioration", J Environ Sci (China), 16(3), pp. 447-453 (2004).*
Kellog et al., "Identification and Hydropathic Characterization of Structural Features Affecting Sequence Specifically for Doxorubicin Intercalation into DNA Double-Stranded Polynucleotides," Nucleic Acids Research, 1998, vol. 26, No. 20, pp. 4721-4732.
Cohen SS., "The Mechanisms of Lethal Action of Arabinosyl Cytosine (araC) and Arabinosyl Adenine (araA)," Cancer, 1977, vol. 40, pp. 509-518, Abstract only.
Abdel-Aziz, W. et al., "Ara-C Affects Formation of Cancer Cell DNA Synthesome Replication Intermediates," vol. 45, p. 312-9, Abstract only, (2000).

(Continued)

*Primary Examiner* — Daniel Sullivan
*Assistant Examiner* — Barbara Frazier
(74) *Attorney, Agent, or Firm* — Venable LLP; Robert Kinberg; Nancy J. Axelrod

(57) ABSTRACT

The present invention relates to compositions comprising a vitamin E analog and an arsenic compound for treating hyperproliferative cells disorders such as cancer. The composition of the invention potentiates arsenic toxicity towards cancer cells and can also prevent arsenic-mediated toxicity of non-cancerous cells.

14 Claims, 21 Drawing Sheets

(56) References Cited

OTHER PUBLICATIONS

Diaz, et al., "Trolox Selectively Enhances Arsenic-mediated Oxidative Stress and Apoptosis in APL and Other Malignant Cell Lines," Blood 2005 (published online Oct. 5, 2004), vol. 105(3) pp. 1237-1348.

Devitek, V. et al., "Cancer: Principle and Practice of Oncology," 2005, vol. 1, 7th Edition, pp. 362-363, 366-367, 373-374.

Miller, WH, Jr., et al., "Mechanisms of Action of Arsenic Trioxide," Cancer Research 62, Jul. 15 2002, pp. 3893-3903.

* cited by examiner

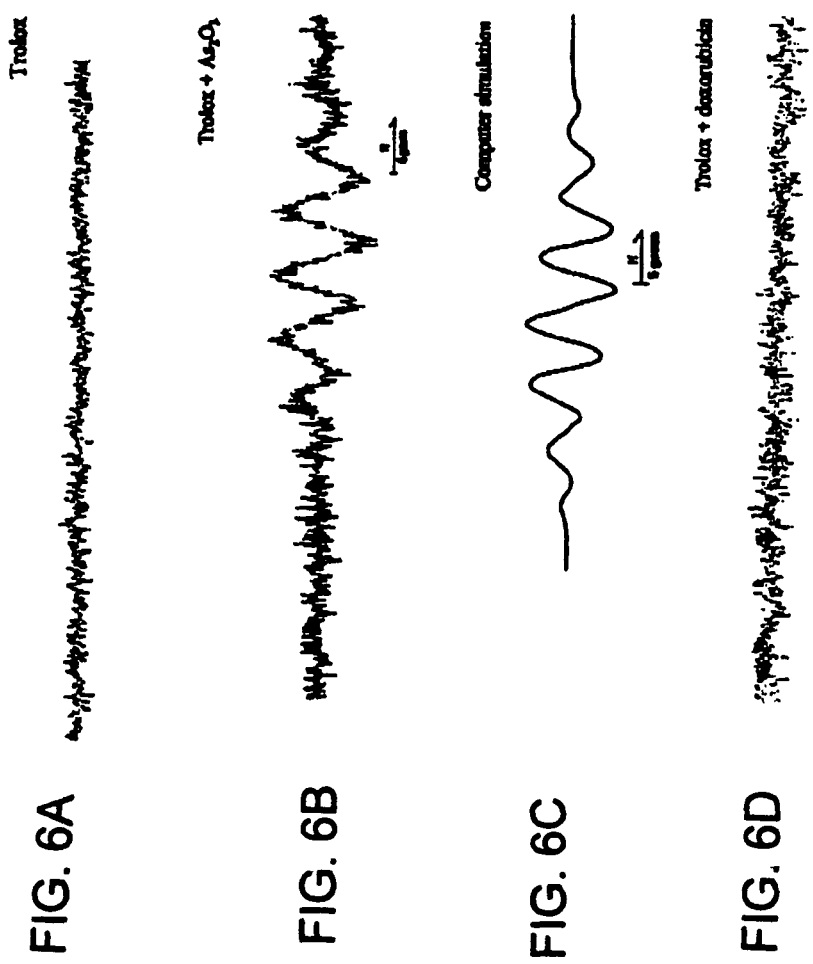

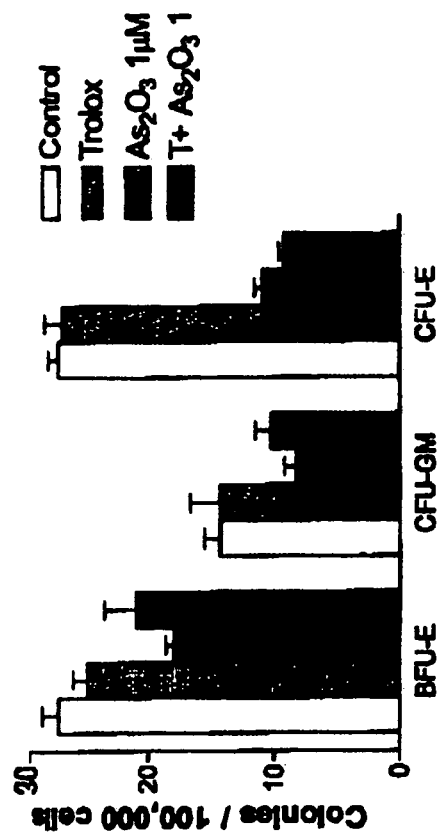
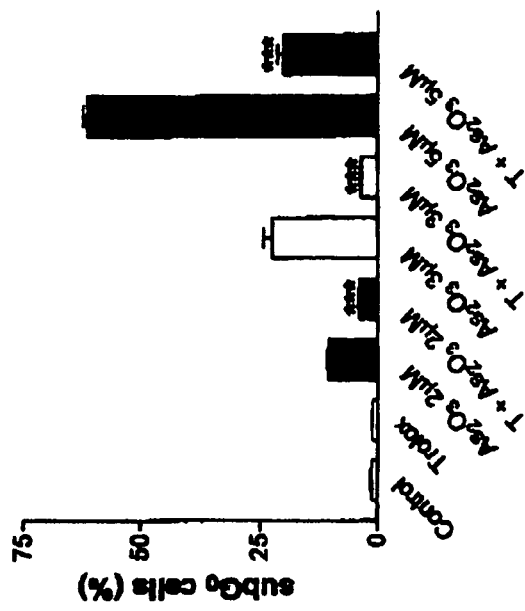
FIG. 7A
FIG. 7B

COMPOSITIONS AND METHODS FOR CANCER TREATMENT

CROSS REFERENCE TO RELATED APPLICATIONS

The present application claims priority to U.S. Provisional Patent Application No. 60/722,970 filed on Oct. 4, 2005, the contents of which are herein incorporated by reference.

FIELD OF THE INVENTION

The present invention relates to compositions comprising arsenic for antineoplastic treatment.

BACKGROUND OF THE INVENTION

Arsenic has been used as a therapeutic agent for more than 2,400 years. Until the 1930s, arsenic was used as a treatment for patients with chronic myelogenous leukemia. More recently, the use of arsenic in leukemia has resurfaced after reports from China that arsenic induced a high remission rate in acute promyelocytic leukemia (APL), including those who were resistant to therapy with all-trans retinoic acid.

The activity of arsenic ($As_2O_3$) in APL is in part related to the disappearance of the PML-RARα fusion protein, the gene product of the chromosomal translocation t(15,17) characteristic of APL, and the induction of differentiation. $As_{23}$ can also induce apoptosis through a variety of mechanisms, which appear to be independent of PML-RARα degradation. In addition to causing mitochondrial toxicity, impairing microtubule polymerization, and deregulating a number of proteins and enzymes through binding to sulfhydryls groups, considerable evidence suggests that $As_2O_3$ induces the accumulation of reactive oxygen species (ROS) and subsequently, induces oxidative stress. Indeed, the intracellular redox status has been shown to be important in predicting whether a cell will respond to arsenic.

Recently it has been shown that $As_2O_3$ stimulates apoptosis in additional malignant cells including acute myeloid leukemia, chronic myeloid leukemia, myeloma and various solid tumor cells. However, higher concentrations of $As_2O_3$ are required to induce apoptosis in non-APL tumor cells, suggesting that higher, more toxic doses might be needed for clinical efficacy. Clinical trials are currently testing arsenic in the treatment of lymphoma and myeloma, but clear evidence of clinical benefit has, thus far, been largely restricted to patients with APL.

It would be highly desirable to increase the therapeutic index of arsenic.

SUMMARY OF THE INVENTION

In accordance with the present invention there is provided compositions comprising a vitamin E analog and an arsenic compound for treating hyperproliferative cells disorders such as cancer.

In another embodiment of the invention there is provided a method for inhibiting hyperproliferative cells in a mammal comprising administering to the mammal a pharmaceutically effective amount of a composition of the invention. There is also provided a method for treating a mammal in need thereof with composition of the invention. In particular, mammals suffering from a neoplastic disease can be treated with a composition of the invention.

In an aspect of the invention vitamin E or analog thereof is used to protect non-cancerous cells from toxicity induced by an arsenic compound.

In yet another embodiment Trolox radicals can be used in cancer treatment of patient in need thereof.

Compositions of the invention can also be used for inducing apoptosis in neoplastic cells, said composition comprising vitamin E or an analog thereof and an arsenic compound.

There is also provided a method for inducing apoptosis in neoplastic cells said method comprising providing neoplastic cells and contacting said cells with a composition of the invention.

For the purpose of the present invention the following terms are defined below.

The term therapeutic index is intended to mean the relative dose/efficacy ratio of a compound or composition.

The term vitamin E broadly encompasses tocopherols and tocotrienols compounds and by vitamin E analogs it is meant derivatives of vitamin E and more particularly derivatives retaining the anti-oxydant properties of Vitamin E. By vitamin E analog it is also meant compounds having a modified phytyl chain. Preferably the modification renders the analog more hydrophilic (i.e. more water soluble). In a preferred embodiment the vitamin E analog is Trolox.

By arsenic compounds it is meant molecules including arsenic in their composition such as monomethyl arsenic, dimethyl arsenic, trimethyl arsenic, arsenic sulfides, arsenic chlorides, arsenic oxides. In a preferred embodiment arsenic is linked to one or more electron affinic atoms, preferably oxygen. Most preferably the molecule used for treating patients in need thereof is arsenic trioxide.

All documents referred herein are hereby incorporated by reference.

Each bar represents an average of three independent samples, and standard deviation bars are shown. Asterisks indicate significant differences from $As_2O_3$-treated cells ( $p<0.01$; * $p<0.001$). (C) Cells were treated as indicated for 48 hours. Caspase 3 activation was measured using Red-DEVD-FMK. Its binding to activated caspase 3 was analyzed by flow cytometry. Asterisks indicate significant differences ($p<0.001$) from $As_2O_3$-treated cells. (D) Western blotting was performed to determine PARP protein levels after 48 hours treatments. β-actin was used to show equal loading of lanes. Results are representative of three independent experiments each performed in duplicate. (E) NB4 cells were treated with doxorubicin, AraC or etoposide with or without trolox (T) for 48 hours. Apoptosis was detected by PI-staining as described above. Each bar represents an average of three independent samples, and standard deviation bars are shown.

Figure 3A:
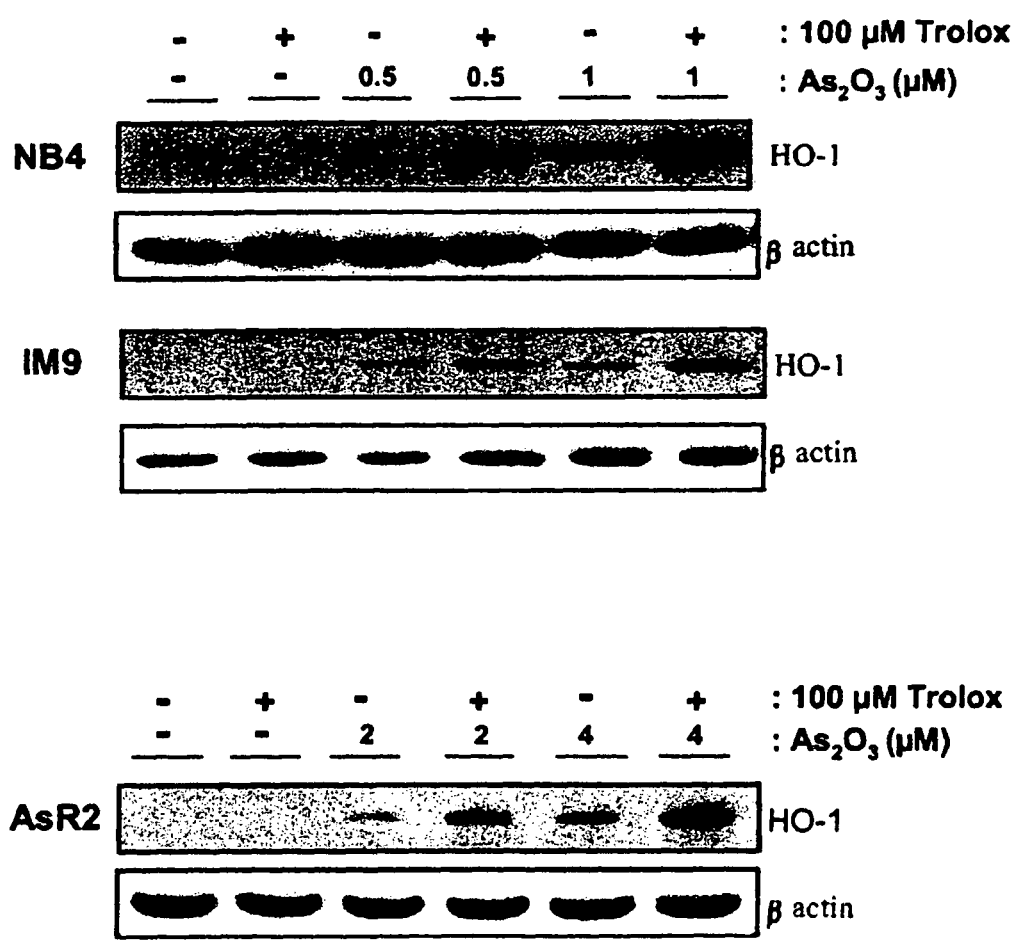
Figure 3C:
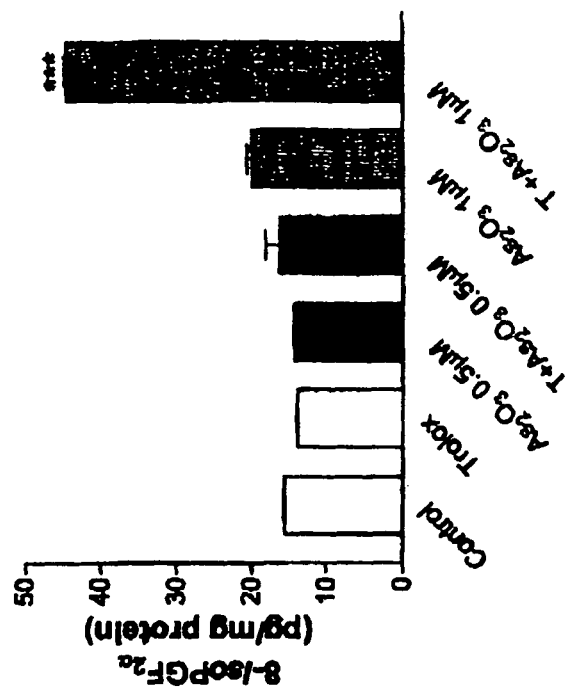

FIG. 3: Trolox potentiates $As_2O_3$-mediated oxidative stress. (A) NB4, IM9 and AsR2 cells were treated with $As_2O_3$ and trolox for 24 hours. Western blot was used to determine HO-1 protein levels. β-actin was used as a loading control. These data represent three independent experiments. (B) Protein carbonyl content was detected by ELISA in NB4 cells treated with $As_2O_3$ alone, trolox or the combination for 3 days with the concentrations indicated. Data depicted are representative of three independent experiments each performed in duplicate. Asterisks indicate significant differences from $As_2O_3$-treated cells. (* $p<0.05$; *** $p<0.001$). (C) $8isoPGF_{2\alpha}$ was detected in whole cells extracts from NB4 cells treated with the indicated compounds for three days. Asterisks indicate significant differences from $As_2O_3$-treated cells ($p<0.001$).

Figure 4:
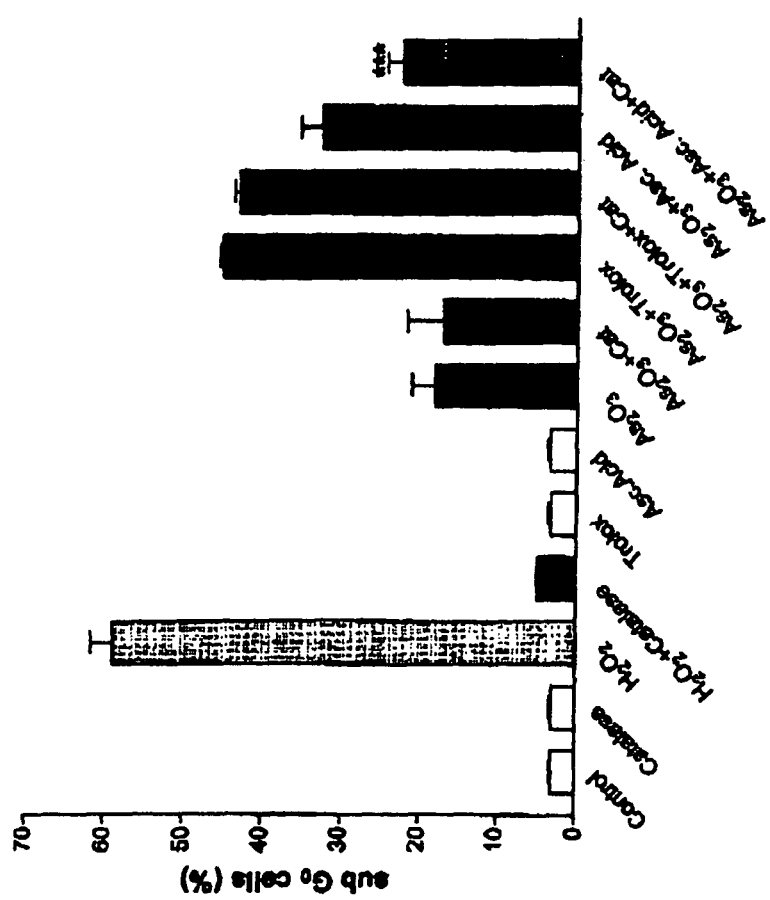

FIG. 4: The synergistic effects of trolox on arsenic-mediated apoptosis are not related to extracellular $H_2O_2$ production. Cells were treated with $As_2O_3$ (1 μM) and trolox or ascorbic acid (100 μM) for 48 hours. Catalase (500U/mL, Cat) was added as indicated to degrade the extracellular $H_2O_2$ generated. Apoptosis was detected by PI-staining, and quantitated by flow cytometric measurement of PI-positive cells. Each bar represents an average of three independent samples, and standard deviation bars are shown. Asterisks indicate significant differences from $As_2O_3$+AA-treated cells ($p<0.001$).

FIG. 5: Trolox enhances $As_2O_3$-mediated JNK activation. Immune complex kinase assays were performed to measure JNK activity with extracts from NB4 (A) or AsR2 cells (B) treated with $As_2O_3$ and trolox for 16 hours as described in materials and methods. Data depicted are representative of three independent experiments.

FIG. 6. Electronic Paramagnetic Resonance detection of the trolox phenoxyl radical. EPR spectra of trolox in the reaction system containing 1 mM Trolox, 5% (v/v) DMSO (A) and $As_2O_3$ 0.02 mM (B) or 0.2 μg/ml doxorubicin (C). (D) Computer simulation of spectrum in (B) obtained using the hyperfine splitting constants: $a^H$ ($CH_3$)=4.56 G; $a^H$ ($CH_3$)=4.86 G; $a^H$ ($CH_3$)=0.23 G; $a^H$ ($CH_2$)=0.37 G; $a^{H'}$ ($CH_2$)=0.76 G.

FIG. 7: The synergistic effects of trolox on arsenic-mediated apoptosis are unique to cancer cells. (A) Normal human PBMC were isolated from three normal donors using a Ficoll gradient. Colony forming ability of PBMC treated with $As_2O_3$ and trolox was assessed by counting CFU-E, CFU-GM and BFU-E after 15 days. Results are representative of three independent experiments each performed in triplicate. (B) Mouse embryonic fibroblasts were treated with $As_2O_3$ with or without trolox for three days. Apoptosis was detected by PI-staining, and quantitated by flow cytometry measurement of PI-positive cells. Each bar represents an average of three independent samples. Asterisks indicate significant differences from $As_2O_3$-treated cells. ($p<0.001$).

Figure 8:
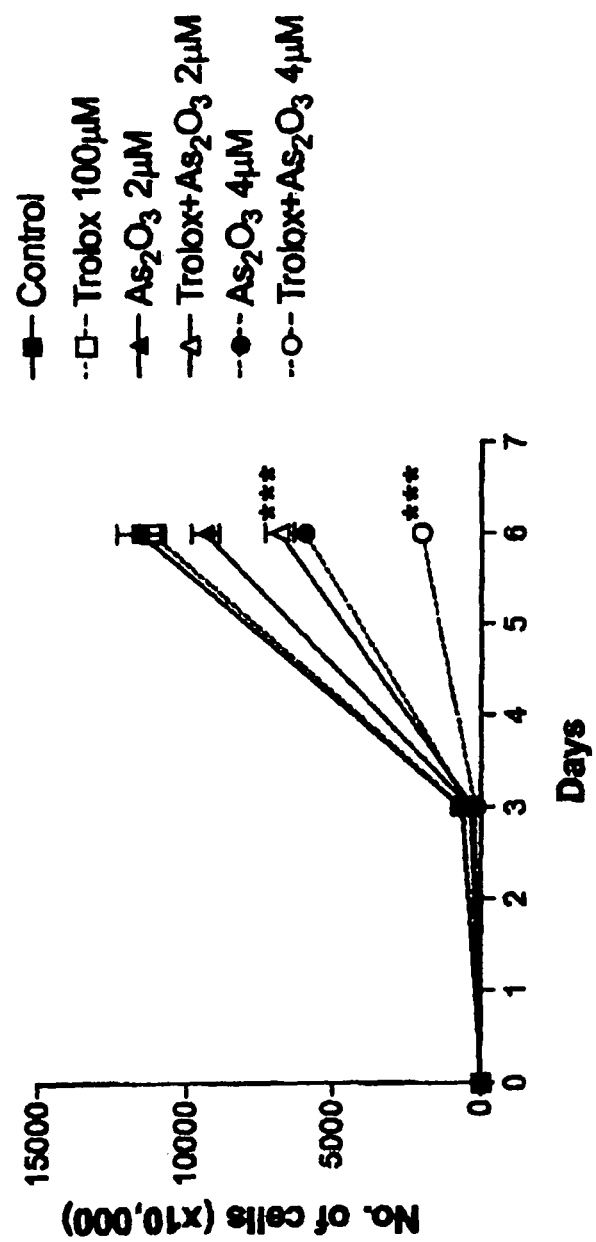

FIG. 8: Trolox enhances $As_2O_3$-induced growth inhibition in murine P388 cells. P388 cells were treated with media (■), Trolox (□), $As_2O_3$ 2 μM (▲), 4 μM (●) and the combination of trolox with $As_2O_3$ 2 μM (Δ) and 4 μM (○). Cell viability was evaluated on day 1, 3, and 6 using trypan blue exclusion. Values are the mean of three independent experiments each performed in triplicates. Standard deviation bars are shown. Asterisks indicate a significant difference ($p<0.001$) from $As_2O_3$-treated cells.

FIG. 9: Trolox enhances arsenic-mediated apoptosis in murine P388 cells. (A) P388 cells were treated with $As_2O_3$ and trolox for 48 hours. Apoptosis was detected by Annexin V-FITC and PI staining. The fluorescent signals of FITC and PI were detected on a FACScan. Apoptotic cells (Annexin V positive/PI negative) were quantified using the CellQUEST software. Each bar represents an average of three independent samples, and standard deviation bars are shown. Asterisks indicate significant differences from $As_2O_3$-treated cells. ($p<0.001$). (B) DNA fragmentation assay, a qualitative index of apoptotic cell death, was performed using agarose gel. (C) Changes in $\Delta\psi_m$ were determined with the fluorochrome JC-1. Data were analyzed and the ratio of mean florescence intensity was calculated. Standard deviation bars are shown. * and *** indicate a significant difference $p<0.05$ and $p<0.001$, respectively from $As_2O_3$-treated cells. (D) S-100 fractions were isolated and cytochrome c release into the S-100 fraction for each condition was assessed by Western blot analysis. β-actin was used to show equal loading of lanes. Results are representative of three independent experiments each performed in duplicate.

FIG. 10 is a schematic representation of the animal experiment design

Figure 10A:
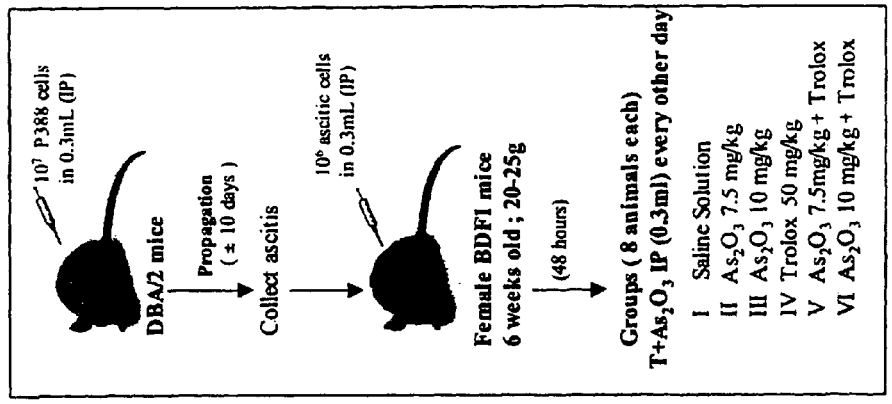

FIG. 11: Trolox protects mice against $As_2O_3$-mediated liver toxicity. Animals were treated as indicated in FIG. 10A. One day after the last dose of arsenic animals were killed and the livers were weighted (A). Blood was collected by cardiac puncture. Serum was separated. Serum activities of alanine aminotransferase (B) and aspartate aminotransferase (C) were assayed using commercially available kits. Standard deviation bars are shown. Asterisk and number sign indicate a significant difference ($p<0.05$) from control group and $As_2O_3$-treated group respectively. (D) Western blot was used to determine HO-1 protein levels. β-actin was used as a loading control. These data represent three independent experiments. Asterisks indicate significant differences from $As_2O_3$-treated group.

Figure 10B:
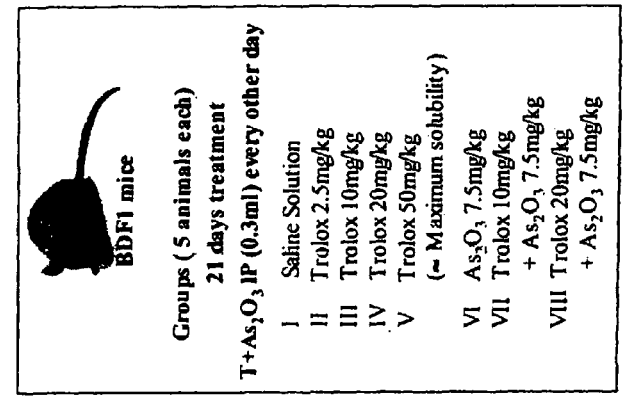

FIG. 12: Trolox increases the life span of BDF1 mice treated with $As_2O_3$. (A)Animals were treated as indicated in FIG. 10B. Percent of survival was calculated and Kaplan-Meyer curve is depicted. Asterisks indicate significant differences from $As_2O_3$-treated groups. (* $p<0.05$; ** $p<0.01$). (B) The increase in life span between the groups was also calculated.

DETAILED DESCRIPTION OF THE INVENTION

In accordance with the present invention, some of the shortcomings associated with the therapeutic use of arsenic have been overcome by the discovery that the therapeutic index of arsenic is significantly increased when arsenic is provided in conjonction with an analog of vitamin E.

It has been particularly found that the compositions of the present invention induce growth inhibition in cancer cells. It has also been found that the compositions of the invention potentiate arsenic mediated apoptosis in cancer cells. Furthermore, the synergistic effect of arsenic and vitamin E analog is specific for cancer cells thereby providing an increased therapeutic index. It has also been found that vitamin E analogs can protect against arsenic-mediated liver toxicity. This beneficial effect provides a mean to increase arsenic doses while keeping side effects to a minimum.

Therapeutic methods of the invention comprise identifying mammalian cells or a mammalian subject presenting neoplastic diasease characteristics and administering to the cells or the subject effective amounts of the composition of the invention.

Thus, pharmaceutical compositions, comprising arsenic and vitamin E or a vitamin E analog, are useful for the treatment of mammals, particularly humans, suffering from neoplastic diseases. More particularly, compositions of the invention are capable of increasing arsenic toxicity towards cells. Compositions of the invention are particularly useful for treating cancer in patients including but not limited to leukemias, lymphomas, myelomas and carcinomas. For example, the composition can be used for treating acute promyelocytic leukemia (APL), multiple myeloma and breast cancer.

The compositions of the present invention can be administered to patients in need thereof for treating neoplasias. The need of a patient for arsenic-vitamin E analog therapy can be determined by those skilled in the art. For example, neoplasias such as the ones mentioned above can be diagnosed by analysis of the blood formula, imaging techniques, detection of cancer specific antigens, physical examination and the like.

The compositions of the invention can be administered with other pharmaceutical compounds or compositions. In particular the compositions of the invention may be administered together with chemotherapeutic drugs to improve their therapeutic ratios.

The compositions can be administered using a pharmaceutically acceptable carrier which can be a preservative solution, a saline solution, an isotonic saline solution, an albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

In accordance with the present invention, the compounds or compositions may be administered to the patient by any biologically suitable route. For example, they may be introduced into the patient by intravenous, subcutaneous, intraperitoneal, intrathecal, intravesical, intradermal, intramuscular, or intralymphatic routes. The compounds or compositions may be in solution, tablet, aerosol, or multi-phase formulation forms. Liposomes, long-circulating liposomes, immunoliposomes, biodegradable microspheres, micelles, or the like may also be used as a carrier, vehicle, or delivery system. The incorporation can be carried out according to known liposome preparation procedures, e.g. sonication and extrusion. Suitable conventional methods of liposome preparation are also disclosed in e.g. A. D. Bangham et al., J. Mol. Biol., 23:238-252 (1965); F. Olson et al., Biochim Biophys. Acta, 557:9-23 (1979); F. Szoka et al., Proc. Nat. Acad. Sci., 75:4194-4198 (1978); S. Kim et al., Biochim. Biophys. Acta, 728:339-348 (1983); and Mayer et al., Biochim. Biophys. Acta, 858:161-168 (1986) all incorporated herein by reference.

The invention should not be limited to any particular method of introducing the compounds into the patient.

It will be appreciated that the actual preferred amounts of active compounds in a given therapy will vary according to the specific compound or composition being utilized, the particular compositions formulated, the mode of application, the particular site of administration, the condition and age of the recipient, etc. Optimal administration rates for a given protocol of administration can be readily ascertained by those skilled in the art using conventional dosage determination tests.

Dosages of arsenic compounds may be generally in the range of about 0.1 to 50 mg/kg body weight. Preferred dosages of arsenic are 0.1 to 10 mg/kg, particularly preferred dosages or arsenic are 1 to 10 mg/kg. Dosages of vitamin E analogs may be generally in the range of about 1 to about 100 mg/kg body weight. Preferred dosages of vitamin E analogs are 5 to 50 mg/kg.

Thus the present invention provides compositions comprising an analog of vitamin E and arsenic for the treatment of neoplastic diseases.

In one embodiment of the invention the combination of vitamin E analogs and arsenic enhances arsenic mediated apoptosis in neoplastic cells. Advantageously, the combination can induce apoptosis in neoplastic cells resistant to arsenic alone. Thus there is also provided a method to induce apoptosis in neoplastic cells by contacting the cells with a composition comprising an arsenic compound and a vitamin E analog.

In another aspect of the invention the vitamin E analogs may be utilized to prevent or reduce the toxicity of arsenic towards non-neoplastic cells. More specifically, vitamin E analogs can reduce the hepatotoxicity of arsenic thereby increasing the therapeutic index of arsenic. This effect is independent of the increase tumor cell killing and can therefore be used for increasing the therapeutic index of arsenic for any arsenic based treatment.

The present invention will be more readily understood by referring to the following examples which are given to illustrate the invention rather than to limit its scope.

EXAMPLE 1

Materials and Methods

Cell Lines

The arsenic trioxide-resistant APL cell line, NB4-M-AsR2 (AsR2), was generated by culturing NB4 cells in the presence of $As_2O_3$ at concentrations that were gradually increased over time[13]. NB4 (provided by Dr. M Lanotte), AsR2 and multiple myeloma IM9 (ATCC) were maintained in RPMI 1640 media. MCF-7 and MDA-231 were obtained from ATCC and maintained in alpha MEM. T47D (ATCC) was cultured in D-MEM/F12. All media were purchased from Life Technologies, Inc and supplemented with 10% fetal bovine calf serum (FBS). AsR2 was routinely grown in RPMI containing 2 μM $As_2O_3$. In experiments examining the response of AsR2, the cells were first washed thoroughly to remove $As_2O_3$, and then cultured 24 hours in media alone prior to initiating the experiment. All cells were grown in a humidified chamber at 37° C. with a 5% $CO_2$ environment.

Growth Assay

NB4, IM9 and AsR2 cells were seeded at $1\times10^5$ cells/ml in 24-well plates. Cells were treated with various concentrations of $As_2O_3$ or doxorubicin, alone or in combination with 100 μM trolox for six days. Viable cells were counted by trypan blue exclusion on day 1, 3 and 6. All cells were maintained at a density lower than $1\times10^6$ cells/ml through dilution as required, and media +/− treatment was replaced every third day. MCF-7, MDA-231 and T47D were seeded in 24-well plates at a density of 4000 cells/well. The next day, fresh media containing $As_2O_3$+/− trolox was added. On the days indicated, cells were fixed in 10% trichloroacetic acid and subsequently stained with sulforhodamine B (SRB). Bound SRB was solubilized in 10 mM unbuffered Tris and optical density was measured at 570 nm in a microplate reader.

Propidium Iodide Staining

Quantitation of apoptotic cells was performed as previously described (Hardin et al. J. Immunol. Methods. 1992; 154:99-107). Cells were treated, washed in buffer (PBS/5% FBS/0.01 M $NaN_3$) at 4° C., pelleted, and resuspended in 0.5 ml of hypotonic fluorochrome solution containing 50 μg/ml propidium iodide (PI), 0.1% sodium citrate, and 0.1% Triton X-100™. Fluorescence was measured on a Becton-Dickinson™ FACS Calibur. Cells undergoing DNA fragmentation and apoptosis (those in which PI fluorescence was weaker than the typical $G_0$-$G_1$ cell cycle peak) were quantified using CellQUEST™ software.

Annexin V Staining

Cells were stained with Annexin-V-FITC and Propidium Iodide in binding buffer according to the manufactures recommendations (BD Pharmigen, San Diego, Calif.). The fluorescent signals of FITC and PI were detected by FL1 at 518 nm and FL2 at 620 nm, respectively, on a FACScan™ (Becton Dickson, San Jose, Calif.). Apoptotic cells (Annexin V positive/PI negative) were quantified using the CellQUEST software.

Western Blotting and Immune Kinase Assays

Cell extracts were washed with cold PBS and resuspended in 0.1 ml lysis buffer (5 mM $NaH_2PO_4$, 1 mM DTT, 10% glycerol, 1 mM PMSF, 10 µg/ml each aprotinin and leupeptin, pH 7.4) at 4° C. Extracts were centrifuged at 14,000 rpm at 4° C., and supernatants were transferred to fresh tubes. Protein concentration was determined with the Bio-Rad™ protein assay (Bio-Rad, Mississauga, Ontario, Canada). To detect HO-1 or PARP, 50 µg of protein was added to an equal volume of 2× sample buffer and run on a 10% SDS-polyacrylamide gel. Proteins were transferred to nitrocellulose membranes (Bio-Rad), stained with Ponceau S in 5% acetic acid to ensure equal protein loading, and blocked with 5% milk in PBS containing 0.5% Triton X-100™ for 1 hour at room temperature. The membrane was hybridized overnight at 4° C. with antibody against PARP (1:1000; Oncogene) or 3 hours with an antibody against HO-1 (1:1000; StressGen). Following three washes with PBS and 0.5% Triton X-100™, blots were incubated with a goat anti-rabbit antibody (1:10,000; PharMingen) for one hour at room temperature. Bands were visualized by enhanced chemiluminescence (Amersham Pharmacia Biotech, Baie d'Urfe, Quebec, Canada). Immunostaining for β-actin was used to confirm equal protein loading. Immune complex kinase assays for c-jun kinase activity were performed as previously described (Davison et al. Blood. 2004; 103: 3496-3502).

Caspase-3 Activity Assay

Activation of caspase-3 was detected using a fluorescent caspase-3 inhibitor, Red-DEVD-FMK™ (Oncogene Research Products, San Diego, Calif.), which irreversibly binds to activated caspase-3 in apoptotic cells. Cells were treated for two days and harvested into microcentrifuge tubes. The cells were incubated with 1 µl of Red-DEVD-FMK™ for 1 hour at 37° C. in 5% $CO_2$. Subsequently, cells were washed twice, resuspended and analyzed by flow cytometry, using the FL-2 channel.

Protein Carbonyls

Oxidized and reduced BSA were prepared and its carbonyl content was quantitated by a colorimetric carbonyl assay described previously (Buss et al. Free Radic Biol. Med. 1997; 23: 361-366). NB4 cells were treated for 3 days with $As_2O_3$, trolox or the combination. Protein samples were adjusted to 4 mg protein/ml. The standards and protein samples were incubated with 3 volumes 10 mM 2,4-dinitrophenylhydrazine (DNP) in 6 M guanidine-HCl, 0.5 M potassium phosphate, pH 2.5 for 45 min at room temperature (mixing every 10-15 min). Aliquots of cell proteins and standards were diluted in PBS and adsorbed to a 96-well immunoplate by incubation overnight at 4° C. After washing with PBS, non-specific sites were blocked with 0.1% Tween 20 in PBS for 1.5 hours at room temperature. After further washing with PBS the wells were incubated with biotinylated anti-DNP antibody (Molecular Probes, 1:10000 dilution) for 1 hour at 37° C. Wells were washed and incubated with streptavidin-biotinylated horseradish peroxidase (Amersham International, 1:3000 dilution), After further washing, o-phenylenediamine/peroxide solution was added. The reaction was stopped after 7 min with 2.5 M sulfuric acid and the absorbance was read with a 490 nm filter. A six point standard curve of reduced and oxidized BSA was incubated with each plate.

Quantification of 8-iso $PGF_{2\alpha}$

NB4 cells were treated for 3 days with $As_2O_3$, trolox or the combination. Cells were washed twice with PBS containing 0.005% BHT, and 10 µg/ml indomethacin. The intracellular and membrane bound 8-iso $PGF_{2\alpha}$, a specific marker for lipid peroxidation, was measured using a competitive ELISA kit from Cayman Chemical Company following the manufacturer instructions.

Detection of Trolox Phenoxyl Radicals and Measurement of Intracellular GSH

Electronic spin resonance spectroscopy reactions contained 0.02 mM $As_2O_3$, 1 mM Trolox, 5% (v/v) DMSO and 0.2 µg/ml doxorubicin. Following the final addition of $As_2O_3$, reaction mixtures were transferred immediately to a quartz ESR flat-cell positioned and pre-tuned within the cavity of a Bruker™ ESP 300 spectrometer using a rapid delivery device and recording commenced using the following instrument settings: modulation frequency, 100 kHz; centre field, 3471.50 G; sweep width, 50.0 G; modulation amplitude, $9.51 \times 10^{-1}$ G; receiver gain, $6.30 \times 10^4$; scan time, 20.97s; time constant, 10.24 msec; power, 20 mW. Spectra was simulated using WinSIM program available for use at the NIEHS/NIH website (hftp://epr.niehs.nih.gov/)[33]. Intracellular reduced GSH levels were assessed enzymatically with glutathione reductase as previously reported (Davison et al. Leukemia. 2003; 17: 931-940).

Peripheral Blood Mononuclear Cell Purification and Colony Forming Unit Assay

Peripheral blood mononuclear cells (PBMC) were obtained from two healthy normal donors after obtaining informed consent and were collected into tubes containing 7.2 mg $K_2$EDTA. The blood was diluted 1:3 in PBS, layered onto an equal volume of Ficoll-Plaque™ PLUS (Amershan Biosciences, Piscataway, N.J.) and centrifuged at 1500 rpm for 30 minutes. The mononuclear cell layer was collected and washed twice in PBS. Methylcellulose media was prepared by combining IMDM, 30% FBS, 1% bovine serum albumin, $10^{-4}$ M 2-mercaptoethanol, 2 mM L-glutamine, 0.1U penicillin, 0.1 µg/ml streptomycin, granulocyte-macrophage colony-stimulating factor (GM-CSF; 10 ng/ml), interleukin-3 (IL-3; 10 ng/ml0) and erythropoietin (EPO; 3U/ml). PBMC were seeded in this media at a concentration of 300,000 cells/ml and treated with or without $As_2O_3$, trolox or the combination. Cultures were performed in triplicate in 35 $mm^2$ dishes and incubated at 37° C. in 4% $CO_2$. Colonies derived from colony-forming units-erythrocyte (BFU-E) and CFU-GM were counted on day 7 and 13.

Statistical Analysis

The significance of data was determined using Prism version 3.0. Analysis of variance followed by Newman-Keuls post-tests were used to determine if cell treatments produced significant changes.

Results

Figure 1A:
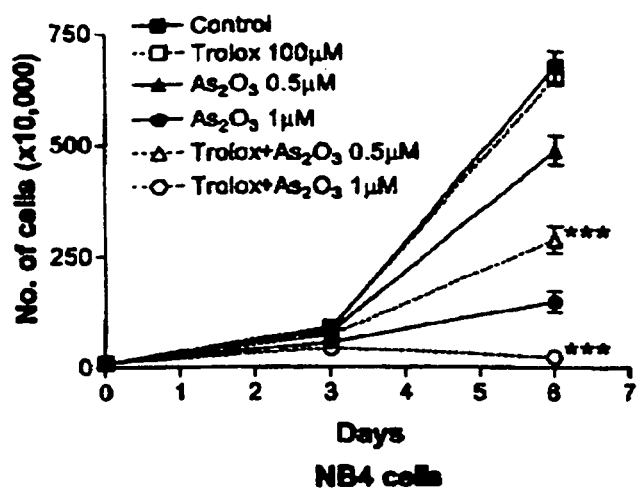
FIG. 1: Trolox enhances $As_2O_3$-induced growth inhibition in NB4, AR2 and IM9 cells. NB4 (A), AsR2 (B) and IM9 cells (C) were treated with trolox, $As_2O_3$ or the combination. Cell viability was evaluated on day 1, 3, and 6 using trypan blue exclusion. Values are the mean of three independent experiments each performed in triplicates. Standard deviation bars are shown. *,  and * indicate a significant difference $p<0.05$, $p<0.01$ and $p<0.001$, respectively from $As_2O_3$-treated cells.
Figure 1B:
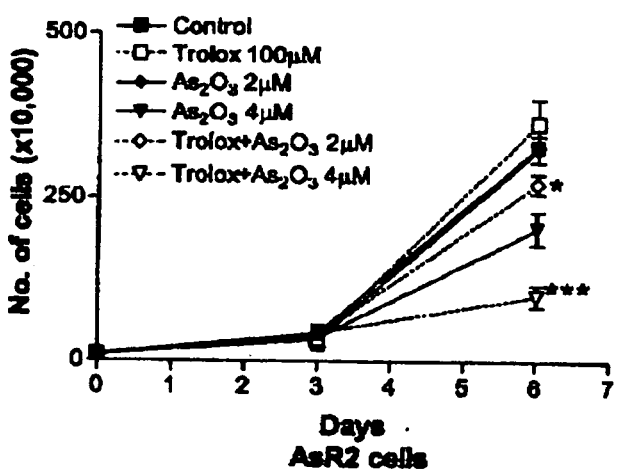
Figure 1C:
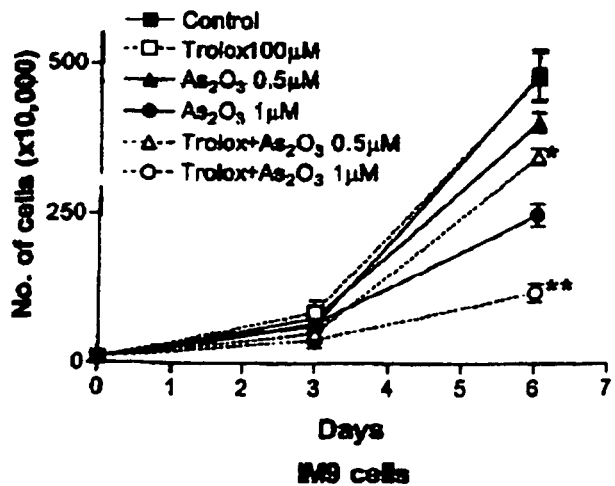

Trolox Significantly Enhances the Inhibitory Effects of $As_2O_3$ on APL, Multiple Myeloma and Breast Cancer Cells We examined the effects of $As_2O_3$ and trolox, both separately and in combination, on the growth of different cell lines. FIG. 1A shows that treatment of NB4 cells for six days with 0.5 or 1 µM $As_2O_3$ reduced viable cell number by 25%±4.7 and 70%±5.6 of control, respectively. 100 µM trolox alone had no effect on cell number at any time point. However, if the cells were treated with 0.5 or 1 µM $As_2O_3$ and 100 µM trolox in combination, 57%±3.5 and 97%±4.2 reductions of cell number were observed. In all cases, trypan blue positive cells were less than 3%. A difference was also seen between $As_2O_3$ and $As_2O_3$+trolox after 72 hours, with 1 µM $As_2O_3$ decreasing cell number by 30% and the combination by 50% ($p<0.001$). We next determined whether trolox could sensitize arsenic-resistant cells. We used an NB4-derived, arsenic-resistant subclone (AsR2), which has an $IC_{50}$ value roughly 10-times higher than its parental NB4 cell line and the multiple myeloma IM9 cell line, which is also less sensitive to $As_2O_3$ than NB4 cells. An enhancing effect of trolox on $As_2O_3$-mediated growth inhibition was observed in both cell lines (FIGS. 1B and C), although trolox did not restore the sensitivity to lower concentrations of $As_2O_3$ in the highly resistant AsR2 cell line. Some solid tumor cells have been shown to be more resistant to $As_2O_3$ than APL cells, so we tested the combined effect of $As_2O_3$ and trolox in breast cancer cell lines. As shown in Table 1, $As_2O_3$-mediated cytotoxicity was enhanced by trolox in all tested cell lines.

TABLE 1

Effect of trolox on $As_2O_3$ mediated growth inhibition in breast cancer cells

| Cell lines | $IC_{50}$ $As_2O_3$ | $IC_{50}$ $As_2O_3$ + Trolox |
|---|---|---|
| MCF-7 | 2.07 ± 0.02 | 1.02 ± 0.09 |
| T47D | 3.22 ± 0.07 | 1.56 ± 0.03 |
| MDA-MB-231 | 2.27 ± 0.08 | 0.98 ± 0.02 |

Cells were treated with 1 µM As2O3 and 100 µM trolox for 3 days. Viable cell number was determined using the trypan blue exclusion method. IC50 indicates concentration of drug needed to inhibit 50% of cell growth. Values are the mean of three independent experiments.

Figure 2A:
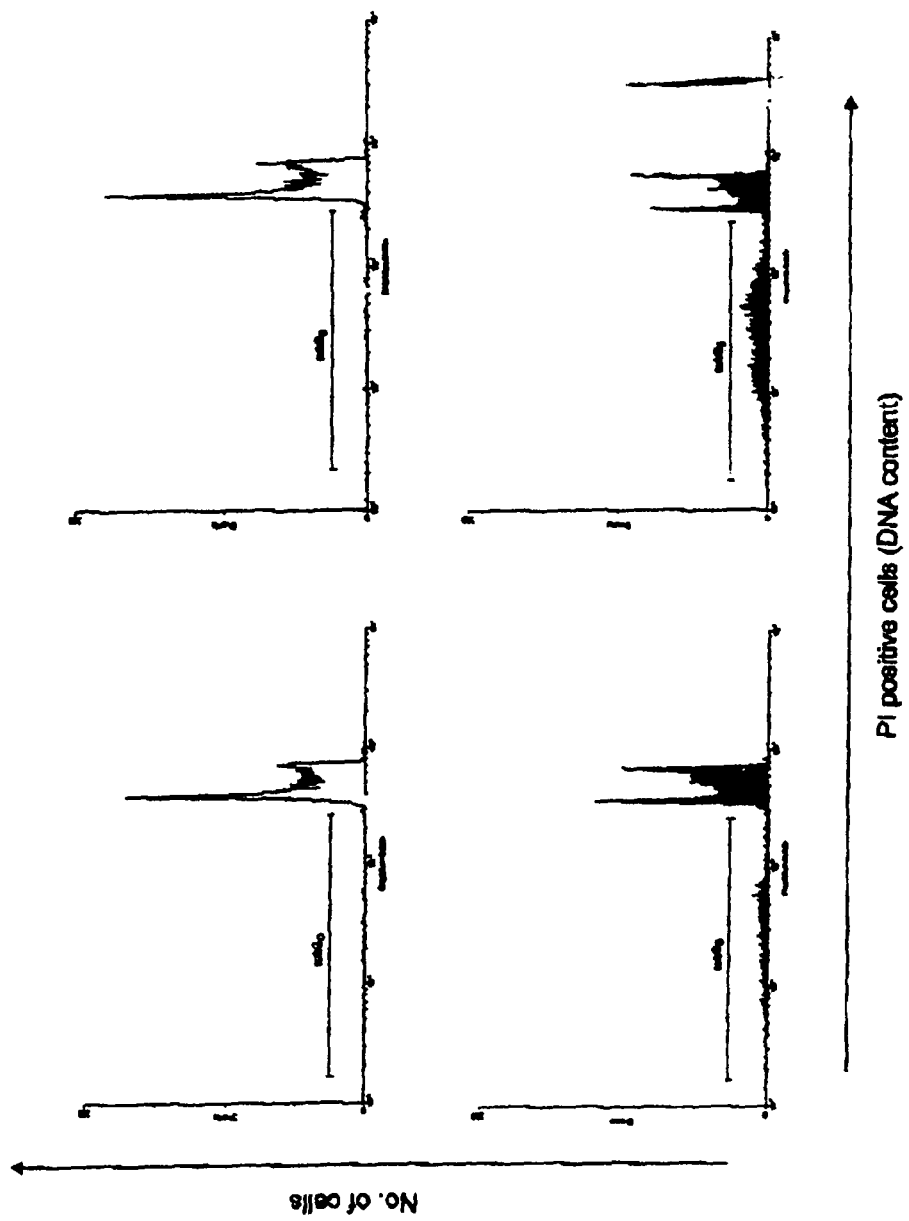
FIG. 2: Trolox enhances arsenic-mediated apoptosis in NB4, AR2 and IM9 cells. (A, B) NB4, AsR2 and IM9 cells were treated with $As_2O_3$ and trolox (T) for 48 hours. Apoptosis was detected by PI-staining. Flow cytometric histograms are shown in (A). Quantitation of PI-positive cells in a hypotonic fluorochrome solution was performed. Apoptotic cells were also stained with Annexin-V-FITC and Propidium Iodide in binding buffer and quantified (B).
Figure 2B:
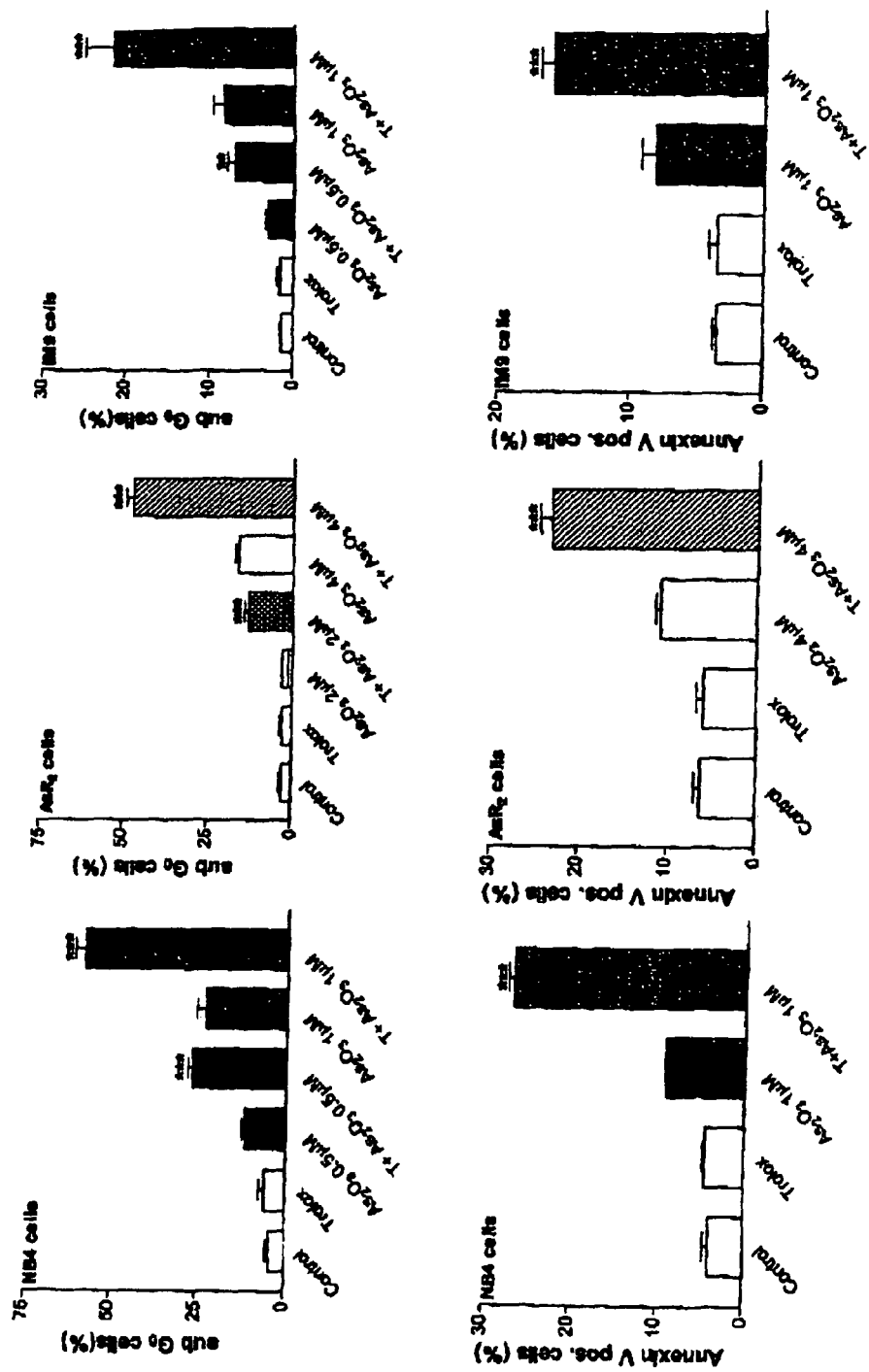
Figure 2C:
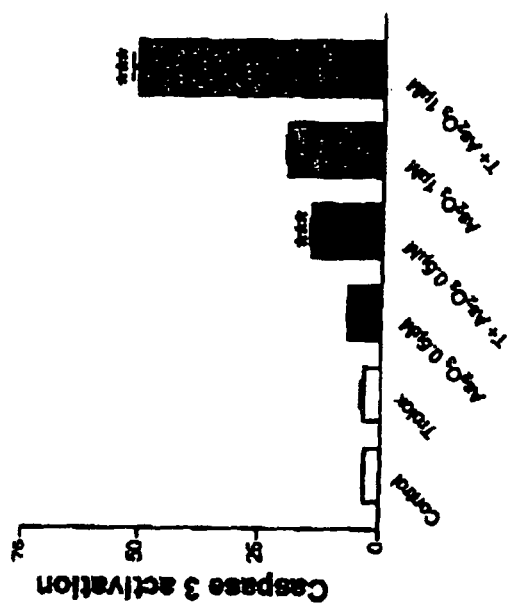
Figure 2D:
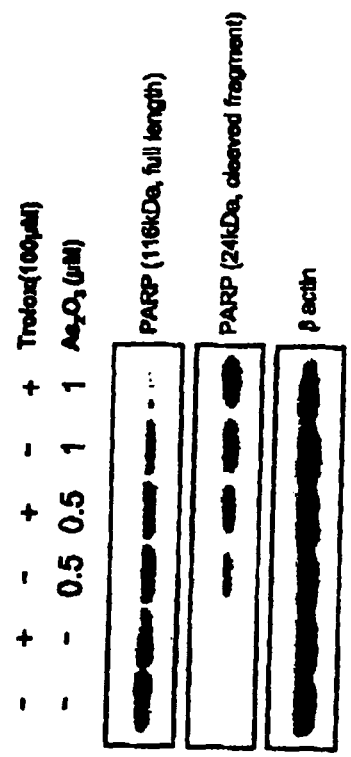
Figure 2E:
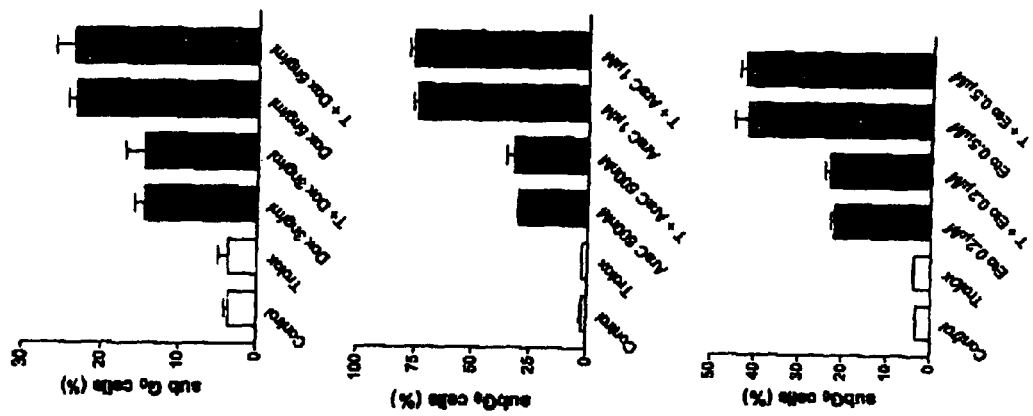

Trolox Enhances $As_2O_3$-Mediated Apoptosis in $As_2O_3$ Sensitive and Resistant Malignant Cells To evaluate whether the growth inhibitory effect observed upon combined treatment of $As_2O_3$ and trolox in NB4, AsR2 and IM9 cells was due to the induction of apoptosis, cells were treated for 48 hours, subsequently stained with PI and analyzed by flow cytometry. As shown in FIGS. 2A and B, trolox enhanced $As_2O_3$-mediated apoptosis in the cell lines studied, at all concentrations of arsenic tested, while trolox alone had no effect on the apoptotic rate. To confirm an enhanced induction of apoptotic death, FITC-labeled Annexin V, which detects phosphatidylserine residues appearing on the external surface of early apoptotic cells, was used. Consistent with the increase in the $subG_0$ subpopulation after PI staining, trolox augmented the percentage of cells positive for Annexin V (FIG. 2B lower panels). To further confirm the induction of apoptosis by the combination of $As_2O_3$ and trolox, we evaluated caspase 3 activation and PARP cleavage. Trolox significantly enhanced the percentage of cells with activated caspase 3 (FIG. 2C) and cleaved PARP (FIG. 2D). These results support the hypothesis that the combined treatment with $As_2O_3$ and trolox induced apoptosis in NB4 cells in a dose dependent fashion. Similar results were obtained with AsR2 and IM9 cells.

Figure 3B:
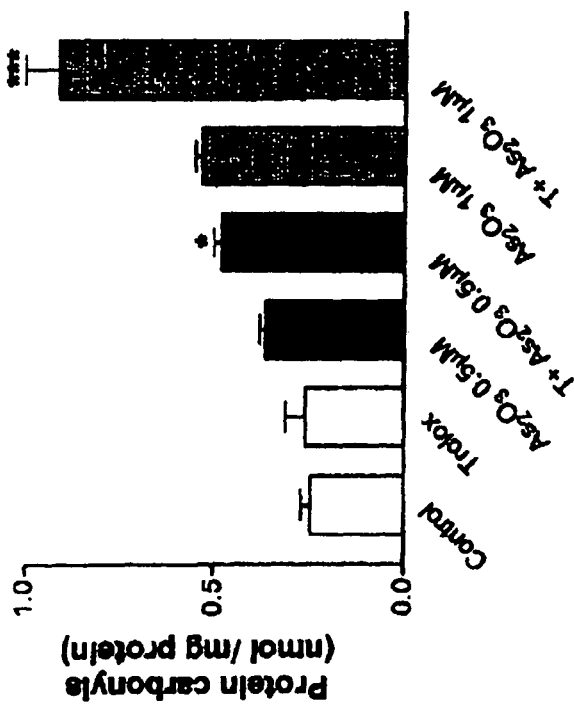

The Combination of $As_2O_3$ and Trolox Results in Increased Cellular Oxidative Stress Oxidative damage has been postulated to be a key mechanism by which arsenic initiates the apoptotic process. Because trolox potentiates $As_2O_3$-induced apoptosis, it is possible that the combination treatment increases cellular oxidative stress. Therefore, we determined whether $As_2O_3$ affected various markers for oxidative stress and whether trolox could augment this effect. Heme oxygenase-1 (HO-1), which is the rate-limiting enzyme for heme degradation and has been widely described as a stress responsive protein, was not detected when trolox was used alone (FIG. 3A). However, the combined treatment markedly enhanced $As_2O_3$-mediated HO-1 induction in all the cell lines tested, suggesting that this combination increased the cellular oxidative stress. To document oxidative damage to cellular components, we analyzed lipids and proteins isolated from NB4 cells treated with $As_2O_3$ or $As_2O_3$+trolox for 3 days. Proteins carbonyls are generated by a variety of mechanism and are sensitive indices of oxidative injury. Isoprostanes are chemically stable prostaglandin-like compounds that are produced independent of the cyclooxygenase (COX) enzyme by free radical-catalyzed peroxidation of arachidonic acid (AA) in situ in membrane phospholipids. F2-isoprostanes are a reliable marker of lipid peroxidation in vivo. FIGS. 3B and C show that $As_2O_3$ alone induces protein oxidation and, to a lesser extent, lipid peroxidation. Oxidative damage to both proteins and lipids was found to be significantly higher when trolox and $As_2O_3$ where combined. Similar results were obtained in AR2 and IM9 cells.

The Cytotoxic Effects Observed When Trolox and $As_2O_3$ Are Combined Are Not Due to Generation of Extracellular $H_2O_2$ Several reports have demonstrated that ascorbic acid (AA), a known antioxidant compound, enhances $As_2O_3$-induced cytotoxicity in multiple myeloma cells. Clement et al. (Clement et al. Antioxid Redox Signal. 2001; 3:157-163), reported that ascorbate-mediated killing in HL60 cells depends on the levels of $H_2O_2$ produced by the reaction of AA within the cell culture medium, and direct addition of $H_2O_2$ to the cells reproduced these results. Further, degradation of extracellular $H_2O_2$ by the addition of catalase, which catalyzes the decomposition of $H_2O_2$ to $H_2O_3$ and $O_2$, blocked any additional toxicity from $AA^{24}$. They concluded that the extracellular $H_2O_2$ generated plays a major role in the synergy observed in vitro by $As_2O_3$ and AA. We asked whether the synergy observed between trolox and $As_2O_3$ was influenced by the generation of extracellular $H_2O_2$. If so, we would expect that the addition of catalase could block the generation of extracellular $H_2O_2$ and consequently decrease the apoptotic rate. Therefore, we treated NB4 cells for three days with $As_2O_3$, trolox, AA and catalase as indicated in FIG. 4. The addition of catalase (500U/ml) prevented the induction of apoptosis by $H_2O_2$, suggesting that even a very large extracellular production of $H_2O_2$ by $As_2O_3$ and trolox could be blocked. Catalase significantly blunted the synergy of $As_2O_3$ with AA, confirming previous reports. In contrast, the addition of catalase did not protect cells treated with $As_2O_3$+trolox.

Trolox Enhances $As_2O_3$-Mediated c-jun Terminal Kinase (JNK) Activation

Figure 5A:
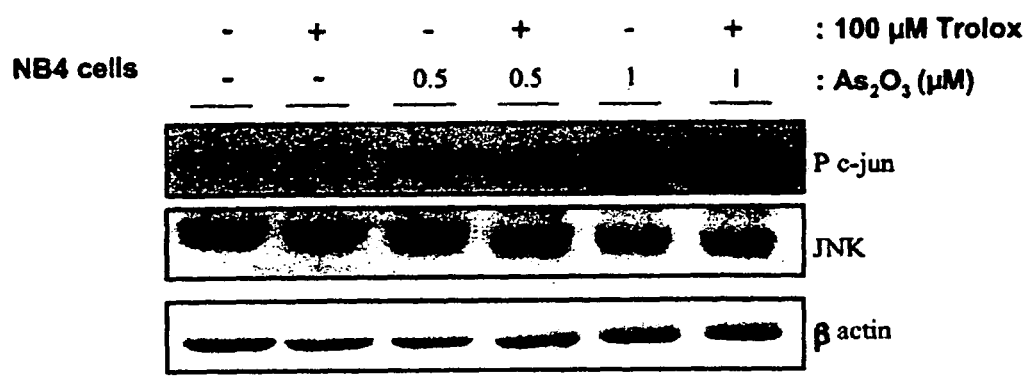
Figure 5B:
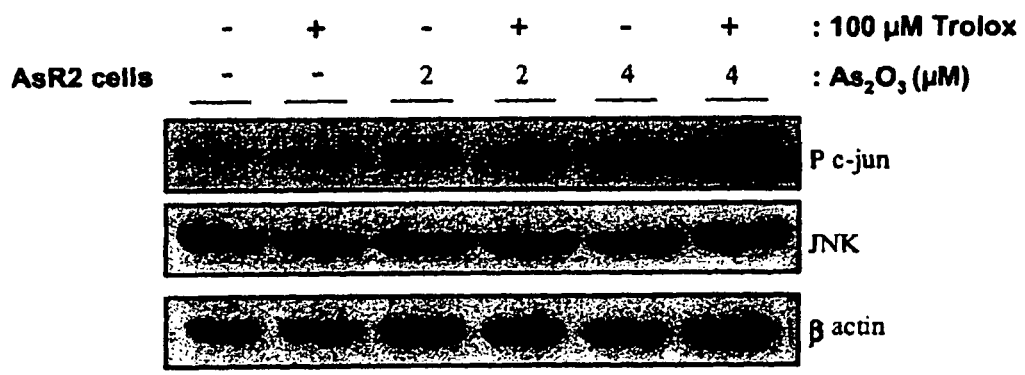

It has been demonstrated that JNK is activated in response to oxidative stress. We have reported that JNK activation is necessary for $As_2O_3$-induced apoptosis of NB4 cell (Davison et al. Blood. 2004; 103: 3496-3502). Therefore, we asked whether the activation of JNK in NB4 cells treated with $As_2O_3$ and trolox for 16 hours might play a role in the synergistic effect of these compounds. We used an immune complex assay with GST-c-jun as an exogenous substrate. FIG. 5A shows that a 24 hour treatment of NB4 cells with as little as 0.5 uM $As_2O_3$ induces significant JNK activation leading to phosphorylation of c-jun. As expected, higher $As_2O_3$ concentrations increased JNK activation. Consistent with the idea that trolox enhances $As_2O_3$-mediated oxidative stress, we observed a further increase in JNK activity when cells are co-treated with $As_2O_3$ and trolox. As expected, the arsenic resistant cell line AsR2 cells showed little activation of JNK following treatment with $As_2O_3$, even at doses sufficient to elicit robust activation of NB4 cells (FIG. 5B). However, when trolox was added to the media, a considerable JNK activation was observed which correlated with apoptotic induction.

$As_2O_3$ Induces the Formation of Trolox Phenoxyl Radicals

Electron paramagnetic resonance (EPR) is an important tool in experimental studies of systems containing unpaired electrons. We used EPR to directly assay the generation of trolox radicals. As shown in FIG. 6B, addition of trolox to reaction mixtures containing $As_2O_3$ resulted in the observation of an intense seven-line EPR signal. The g-value (3477.530 G), the relative intensities, and the splittings all confirm the presence of the trolox phenoxyl radical. Its identity is further confirmed by the simulated spectrum (FIG. 6C), which is based on the published coupling constants for this radical. This signal is not generated by trolox alone (FIG. 6A) nor in the presence of doxorubicin (FIG. 6D) suggesting the requirement of $As_2O_3$ and its hydration products for the formation of this radical.

Trolox Does Not Potentiate $As_2O_3$ Effects in Non-Malignant Cells

We sought to determine the effects of $As_2O_3$ combined with trolox in normal human hematopoietic colony forming cells and mouse embryonic fibroblasts. Normal human PBMCs were isolated, grown in methylcellulose, and treated with $As_2O_3$, trolox or the combination for 2 weeks. FIG. 7A shows that 1 µM of $As_2O_3$ inhibited CFU-E by approximately 62%, but had minimal effect on CFU-GM or BFU-E colony formation. Treatment with trolox alone did not inhibit colony formation and trolox did not enhance $As_2O_3$-inhibition of CFU-GM, BFU-E or CFU-E. Mouse embryonic fibroblasts were treated with different concentrations of $As_2O_3$ for three days, stained with PI and analyzed by flow cytometry. Interestingly, trolox significantly decreased $As_2O_3$-mediated apoptosis at all doses studied (FIG. 7B).

EXAMPLE 2

Materials and Methods
Reagents.

$As_2O_3$ and Trolox, were purchased from Sigma Chemical (St Louis, Mo.). $As_2O_3$ was dissolved in 0.4N NaOH and then diluted in phosphate-buffered saline (PBS). Trolox was resuspended in dimethylsulfoxide (DMSO) at a stock solution of 0.1 mol/L. The final DMSO concentration in the medium was not greater than 0.1%.

Cell lines

P388 was kindly provided by Dr. Dai Jing, Department of Medicine, Mount Sinai Medical Center, New York, and was maintained in DMEM (Life Technologies,Bethesda, Md.) supplemented with 10% fetal bovine calf serum (FBS). Cells were grown in a humidified chamber at 37° C. with a 5% CO2 environment.

Growth Assays

P388 cells were seeded at $1\times10^5$ cells/ml in 24-well plates. Cells were treated with various concentrations of $As_2O_3$ alone or in combination with 100 µM trolox for six days. Viable cells were counted by trypan blue exclusion on day 1, 3 and 6. All cells were maintained at a density lower than $1\times10^6$ cells/ml through dilution as required, and media +/− treatment was replaced every third day.

Annexin V/Propidium Iodide Staining

Cells were stained with Annexin-V-FITC and Propidium Iodide in binding buffer according to the manufactures recommendations (BD Pharmigen, San Diego, Calif.). The fluorescent signals of FITC and PI were detected by FL1 at 518 nm and FL2 at 620 nm respectively on a FACScan (Becton Dickson, San Jose, Calif.). Apoptotic cells (Annexin V positive/PI negative) were quantified using the CellQUEST software.

DNA Fragmentation Analysis

DNA fragmentation assay, a qualitative index of apoptotic cell death, was performed using agarose gel electrophoresis. Cells ($2\times10^6$) were fixed with 70% ethanol, stored at −20° C. for 24 h and collected by centrifugation. Degraded oligonucleosomal DNA was extracted with 40 µL of phosphate-citric acid buffer at room temperature for 1 h and vacuum dried for 15 min. The powder was resuspended in 3 µL of 0.25% Nonidet P-40 and 3 µL of 1 mg/mL RNase and then incubated at 37° C. for 30 min. Three µL of 1 mg/mL proteinase K was added to the solution and incubated at 37° C. for another 30 min. The mixture, together with 12 µL of loading buffer, was loaded on a 0.8% agarose gel containing 0.5 mg/mL ethidium bromide and electrophoresed at 2 V/cm overnight. The DNA laddering was recorded with a Chemilmager 4000 image analyser (Alpha Innotech Corporation, San Leandro, Calif., USA).

Detection of the Mitochondrial Membrane Potential ($\Delta\psi_m$)

Changes in $\Delta\psi_m$ were determined with the J-aggregate-forming lipophilic cationic fluorochrome 5,5',6,6'-tetrachloro-1,1',3,3'-tetraethylbenzimidazolylcarbocyanine iodide (JC-1; Molecular Probes, Eugene, Oreg.). JC-1 loading into mitochondria is detected by a shift in fluorescence from green, which is characteristic of its monomeric form, to orange, which reflects its aggregation in mitochondria. Cells were incubated with 2.5 mg/mL JC-1 (dissolved in DMSO) for 15 min at room temperature in darkness. After centrifugation for 5 min at 1200 rpm, cells were washed twice with PBS at 4° C., resuspended in 0.5 mL PBS, and analyzed on a FACSCalibur flow cytometer. Data were analyzed with the computer software CELLQuest (Becton Dickinson) to quantify the percentage of red (polarized) and green (depolarized) fluorescence. The ratio of mean florescence intensity (MFI) between FL1 and FL2 was also calculated for each tested sample. For a positive control in the assay, calcium ionophore was used to induce mitochondrial depolarization to nearly 100 percent.

Preparation of S-100 Fractions and Assessment of Cytochrome c Release

P388 cells were harvested after drug treatment by centrifugation at 1200 rpm for 10 min at 4° C. The cytosolic S-100 fraction was prepared as described previously, with minor modifications. Cell pellets were washed once with ice-cold phosphate-buffered saline (PBS) and resuspended in 5 volumes of buffer (75 mM NaCl, 8 mM $Na_2HPO_4$, 1 mM $NaH_2PO_4$, 1 mM EDTA, 350 ug/ml digitonin, 1 mM dithiothreotol, 0.1 mM phenylmethylsulfonyl fluoride, 10 µmol/L aprotinin and 10 µmol/L leupeptin). After chilling for 30 minutes on ice, the cells were disrupted by 15 strokes of a glass homogenizer. The homogenate was centrifuged twice to remove unbroken cells and nuclei (750 g, 10 min, 4° C.). S-100 fractions (supernatants) were then obtained by centrifugation at 100,000 g, 60 min at 4° C. All steps were performed on ice or at 4° C. Cytochrome c release into the S-100 fraction for each condition was assessed by Western blot analysis of the resulting fractions as detailed below.

Western Blotting

Cells were washed with cold PBS and resuspended in 0.1 ml lysis buffer (5 mM $NaH_2PO_4$, 1 mM DTT, 10% glycerol, 1 mM PMSF, 10 µg/ml each aprotinin and leupeptin, pH 7.4) at 4° C. Extracts were centrifuged at 14,000 rpm at 4° C., and supernatants were transferred to fresh tubes. Protein concentration was determined with the Bio-Rad protein assay (Bio-Rad, Mississauga, Ontario, Canada). Livers from treated mice were disrupted by 2-4 sec bursts of a Polytron homogenizer. Cell debris was removed by centrifugation at 700 g for 15 min, followed by centrifugation of the supernatant twice at 14,400 g for 15 min and finally at 100,000 g for 1 h at 4° C. Proteins were separated and probed as described previously (Diaz et al. Blood. Feb. 1, 2005, Vol. 105, Number 3). The source and dilution of antibodies were as follows: cytochrome c, 1:500, Clontech; HO-1, 1:1000, Stressgen; βActin 1:10,000, Sigma. Following three washes with PBS and 0.5% Triton X-100, blots were incubated with a horseradish peroxidase-conjugated secondary antibody (1:10,000; PharMingen) for one hour at room temperature. Bands were visualized by enhanced chemiluminescence (Amersham Pharmacia Biotech, Baie d'Urfe, Quebec, Canada). Immunostaining for β-actin was used to confirm equal protein loading.

In vivo Toxicity Experiments

BDF1 mice were obtained from Charles River Laboratories (Wilmington, Mass.). All procedures confirmed to the Canadian Institute for Health Research guidelines for the care and use of laboratory animals. Mice were randomly divided into eight groups each with six mice. Each group received Trolox (2.5, 10, 20 and 50 mg/kg) and $As_2O_3$ (7.5 mg/kg) alone or in combination intraperitoneally every other day for fourteen times. Animals were weighted every other day. One day after the last dose of arsenic, blood was collected by cardiac puncture. Serum was separated after allowing the blood to coagulate at room temperature for 2 h. Total protein levels, glucose content, serum activities of alanine aminotransferase (ALT), aspartate aminotransferase (AST) and alkaline phosphatase (AKP) were assayed using commercially available kits. Mice were sacrificed by cervical dislocation, followed by decapitation. Liver and kidney were extracted and washed in ice-cold isotonic saline solution to remove debris and blood. Livers were weighted using an analytic balance. A representative portion of all the extracted organs were fixed in 10% neutral-buffered formalin and embedded in paraffin for histological analysis. The rest was frozen in liquid nitrogen for biochemical assays.

In vivo Anti-Tumor Experiments

Transplantable P388 cells were injected intraperitoneally in DBA/2 mice (Charles River Laboratories, Wilmington, Mass.) and allowed to growth for fifteen days. Cells were collected from the peritoneum, washed and resuspended in PBS. For experiments, 0.1 mL containing $2 \times 10^6$ cells obtained from the ascites was inoculated intraperitoneally in BDF1 mice. Mice were randomly divided into six groups each with eight mice. After 24 hours, each group was given saline, $As_2O_3$ (7.5 or 10 mg/kg), and trolox (50 mg/kg) alone or in combination intraperitoneally every other day for thirty times. The percentage increase in lifespan over control (ILS) was calculated as follows: ILS%=(T-C)/C×100, where T is the test mean survival time, and C is the control mean survival time.

Statistical Analysis

The significance of data was determined using Prism version 3.0 (GraphPad software, San Diego, Calif.). Analysis of variance followed by Newman-Keuls post-tests were used to determine if treatments produced significant changes.

Results

Trolox Increases the Growth Inhibitory Effects of $As_2O_3$ in Murine Lymphoma P388 Cells Our laboratory has previously documented that Trolox increases $As_2O_3$-mediated growth inhibition in a variety of cell lines. In the present study we investigated whether this combination have similar effects in lymphoma cells. As FIG. 8 illustrates, $As_2O_3$ was able to induce a dose dependent growth inhibition in the murine lymphoma cell line P388. This cell line is less sensitive to $As_2O_3$ than some leukemic cell lines where 0.5 uM and 1 uM $As_2O_3$ are sufficient to induce a similar effect. However, when Trolox was combined with 2 or 4 uM of $As_2O_3$, 25 and 47% growth inhibition were observed. These results indicate that this combination is also effective in this cell line.

Trolox Enhances $As_2O_3$-Induced Apoptosis in P388 Cells.

To further study the growth inhibitory effect observed when this combination was used we used conventional techniques to establish the ability of this cell line to undergo apoptosis.

Figure 9A:
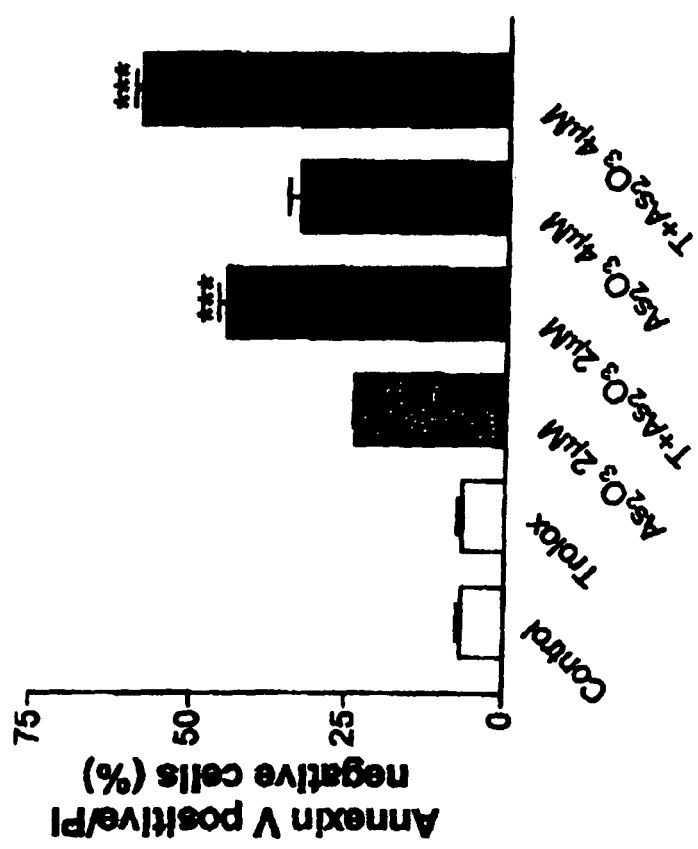
Figure 9B:
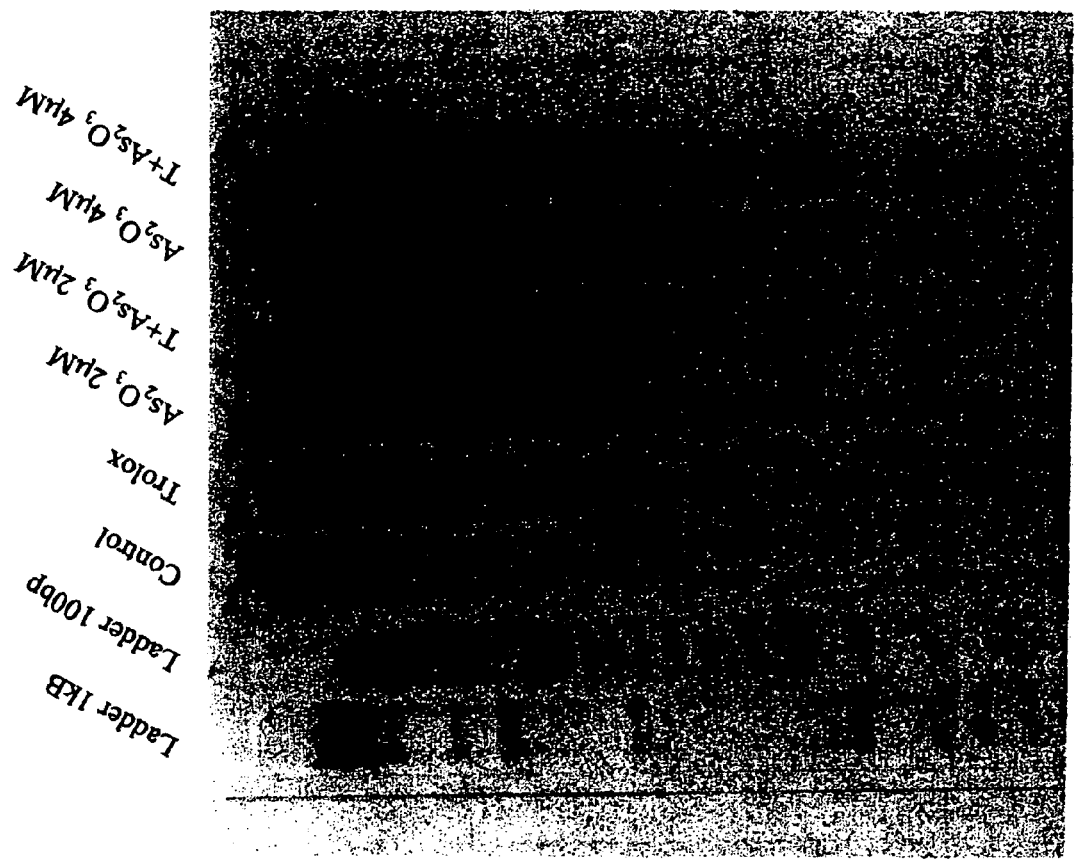

We use a combined staining with Annexin V and Propidium Iodide to discriminate between viable (Annexin V-negative/PI-negative), apoptotic (Annexin V-positive/PI-negative), and necrotic (Annexin V-positive/PI-positive) cells. As depicted in FIG. 9A approximately 25% of P388 cells were apoptotic. This effect was increased to 45% when Trolox was added to the culture media. Similar effects were observed at 4 uM. Consistent with these results, we observed an increase in DNA fragmentation when the combination was used at the two doses studied (FIG. 9B.)

Figure 9C:
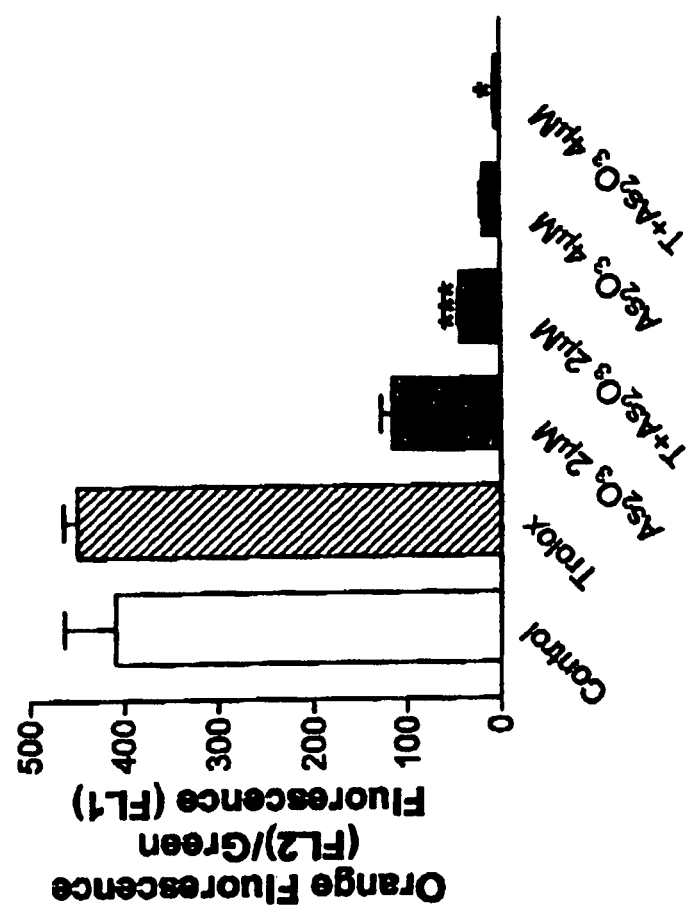
Figure 9D:
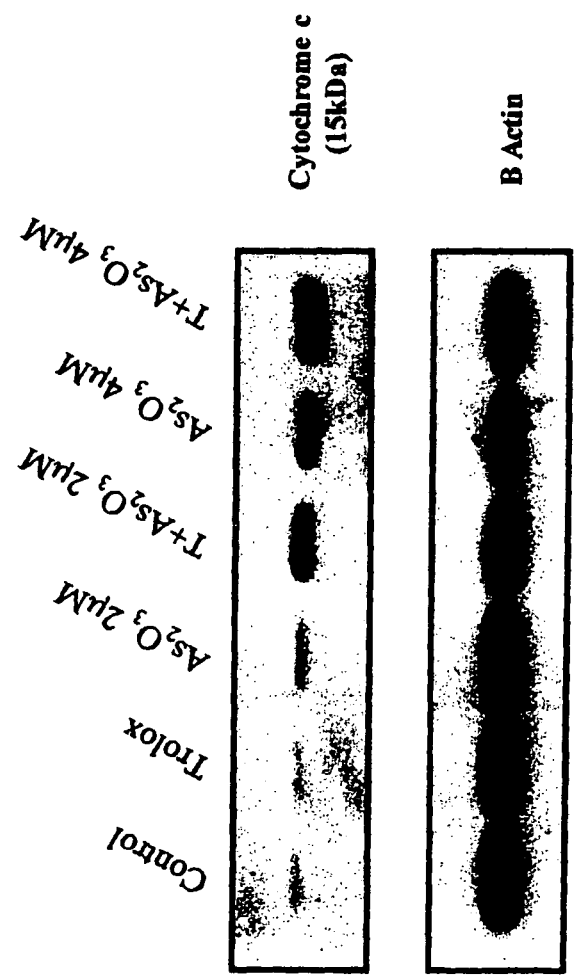

It is generally accepted that the apoptotic pathway is related to a breach in the mitochondrial integrity such that the usually impermeable inner mitochondrial membrane becomes permeable to the nonspecific passage of ions and small molecules, causing complete loss (depolarization) of the transmembrane potential. We employed the fluorescent dye JC-1, which exhibits potential dependent accumulation in mitochondria, to determine the effect of $As_2O_3$ and Trolox on mitochondria permeability in P388 cells. As depicted in FIG. 9C, a decrease in the ratio of red to green fluorescence was observed in the $As_2O_3$-treated cells in a dose dependent manner compared to control which indicatives mitochondrial depolarization. One of the small molecules that are released when the membrane potential is compromised is cytochrome c. As shown in FIG. 9D, an increase in cytoplasmic cytochrome c content was observed when Trolox and arsenic were used in combination at all the doses studied.

Thus, using a variety of complementary techniques, our data indicate that trolox increases $As_2O_3$-induced apoptosis in P388 cells.

Trolox Decreases $As_2O_3$-Mediated Toxicity in BDF1 Mice

In our previous work we demonstrated that trolox does not enhance cytotoxicity of $As_2O_3$ in colony forming assays using human hematopoietic peripheral blood mononuclear cells and in mouse embryo fibroblasts. This suggests that cytotoxic enhancement accruing from trolox exposure could be specific to tumor cells.

We have now extended these in vitro results to in vivo studies. Toxicological studies were conducted to define the maximum tolerable dose of trolox in BDF1 mice and the toxicity associated with the combination of $As_2O_3$ and trolox. The selected arsenic dose (7.5 mg/kg) had been previously used in rat and other mouse strains and identified in the literature as well tolerated and efficacious.

Considering the low toxicity of trolox, and the lack of synergy we observed between this drug and $As_2O_3$ in non-malignant cells, we asked whether trolox could decrease $As_2O_3$-associated liver toxicity in vivo. Mice were randomly divided into six groups each with six mice. Each group received trolox (10 or 20 mg/kg) and $As_2O_3$ 7.5 mg/kg alone or in combination (FIG. 10A). None of the animals exhibited discomfort or obvious distress throughout the duration of the experiment. No differences in weight were observed at the endpoint of the experiment in any of the treated groups compared to control.

The liver has been reported to be susceptible to arsenic-induced damage, marked by tissue necrosis and other histological as well as biochemical changes in different animal models. Liver damage as a consequence of arsenic poisoning has also been reported in human subjects. Consistent with this literature, we observed arsenic-induces liver toxicity in this experiment.

Figure 11A:
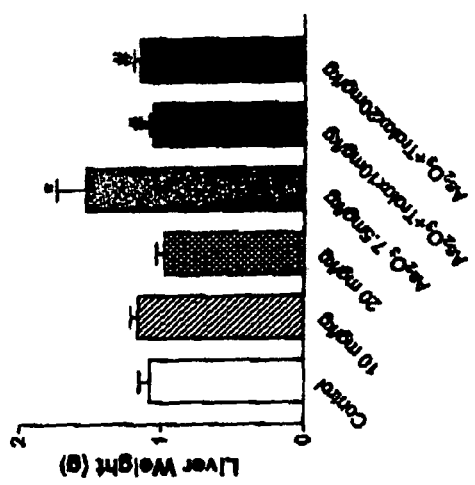
Figure 11C:
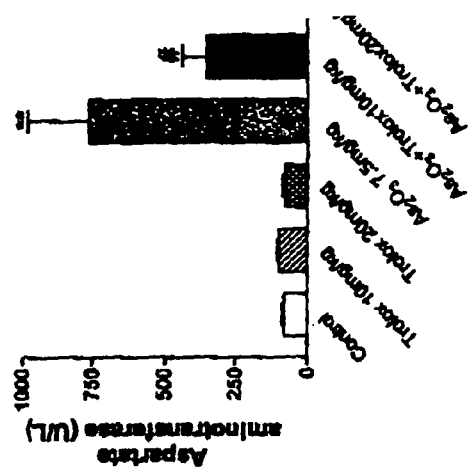
Figure 11B:
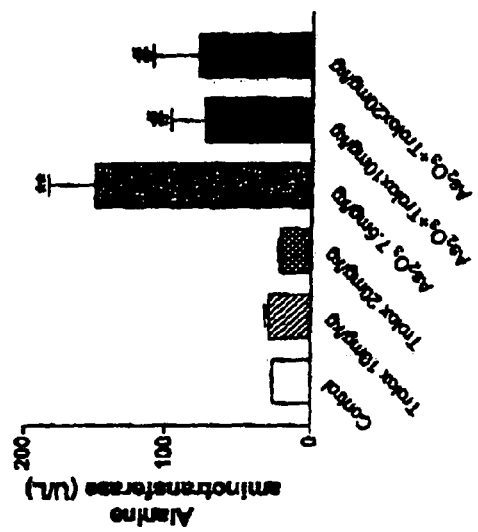

As depicted in, FIG. 11A, moderate hepatomegaly was observed in the $As_2O_3$-treated group. However, in the groups treated with the combination of $As_2O_3$ and trolox, the hepatomegaly was completely reduced.

Aspartate aminotrasferase (AST) and alanine aminotransferase (ALT) levels in blood are common means of detecting liver damage, the enzymes being raised several fold in the first 24 hours after damage. AST and ALT activities were increased in the $As_2O_3$-treated group by 4.2 and 3.5 fold compared to the control group respectively. However in the animals treated with the combination of $As_2O_3$ and either 10 or 20 mg/kg Trolox, a significant reduction of AST and ALT activities were observed ($p<0.05$). The activity of alkaline phosphatase, an indication of cholestasis, was not significantly affected by any of the treatments (data not shown), which suggests that $As_2O_3$ can induce a direct injury to the hepatocytes without blocking bile excretion. We did not observe any change in glucose or total protein levels in any of the groups.

Figure 11D:
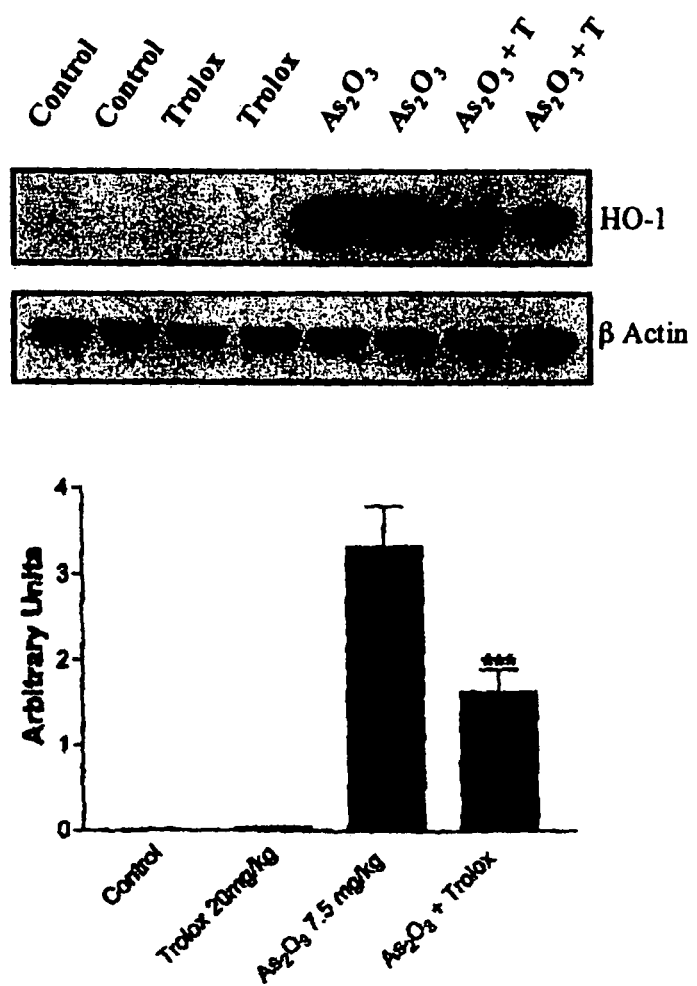

To explore the mechanism by which Trolox significantly decreases markers for liver toxicity and hepatocellular death or necrosis, we analyzed the expression of heme oxygenase-1 (HO-1), which is widely accepted as a sensitive and reliable marker of cellular oxidative stress. As depicted in FIG. 11D, $As_2O_3$ increases oxidative stress in the liver of the treated mice. The addition of trolox induced a significant decrease in HO-1 protein expression suggesting restoration of the hepatocellular redox homeostasis.

Thus, we have shown that arsenic treatment induces toxicity in mice, as evidenced from the induction of hepatomegaly and alterations in the enzymatic activities of AST and ALT. The addition of trolox reduces these arsenic toxicities.

Figure 12A:
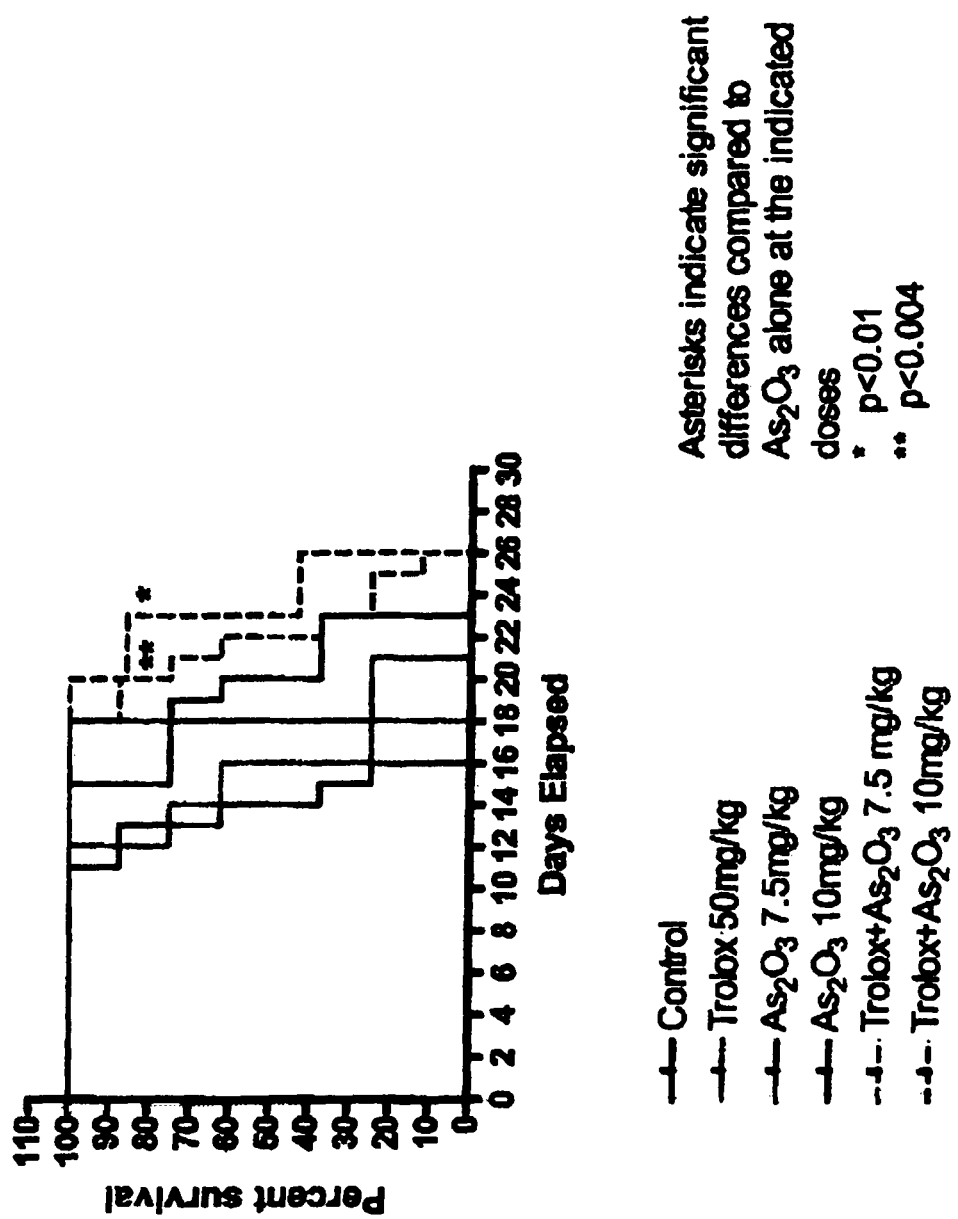

Trolox Increases $As_2O_3$-Mediated Antitumor Effects in BDF1 Mice Bearing Lymphoma P388 Cells On the basis of the in vitro potency and favorable in vivo toxicity, $As_2O_3$ and trolox were evaluated for an in vivo antitumor efficacy in mice bearing P388 murine lymphoma tumors. P388 cells were injected intraperitoneally in BDF1 mice. Animals were randomly divided in six groups and injected with saline solution, $As_2O_3$, alone or in combination with trolox (FIG. 10B.) Based on low preliminary toxicity at 7.5 mg/kg dose, arsenic was given at 7.5 and 10 mg/kg and trolox at 50 mg/kg, which was not toxic but approached the maximum solubility. As shown in FIG. 12A, $As_2O_3$ treatment prolonged survival, with median survival times of 20 and 18 for $As_2O_3$ 7.5 mg/kg and 10 mg/kg respectively ($p<0.001$). The median survival time when the animals were treated with the combination of $As_2O_3$ and trolox was further prolonged to 24.5 and 22 ($p<0.001$).

Figure 12B:
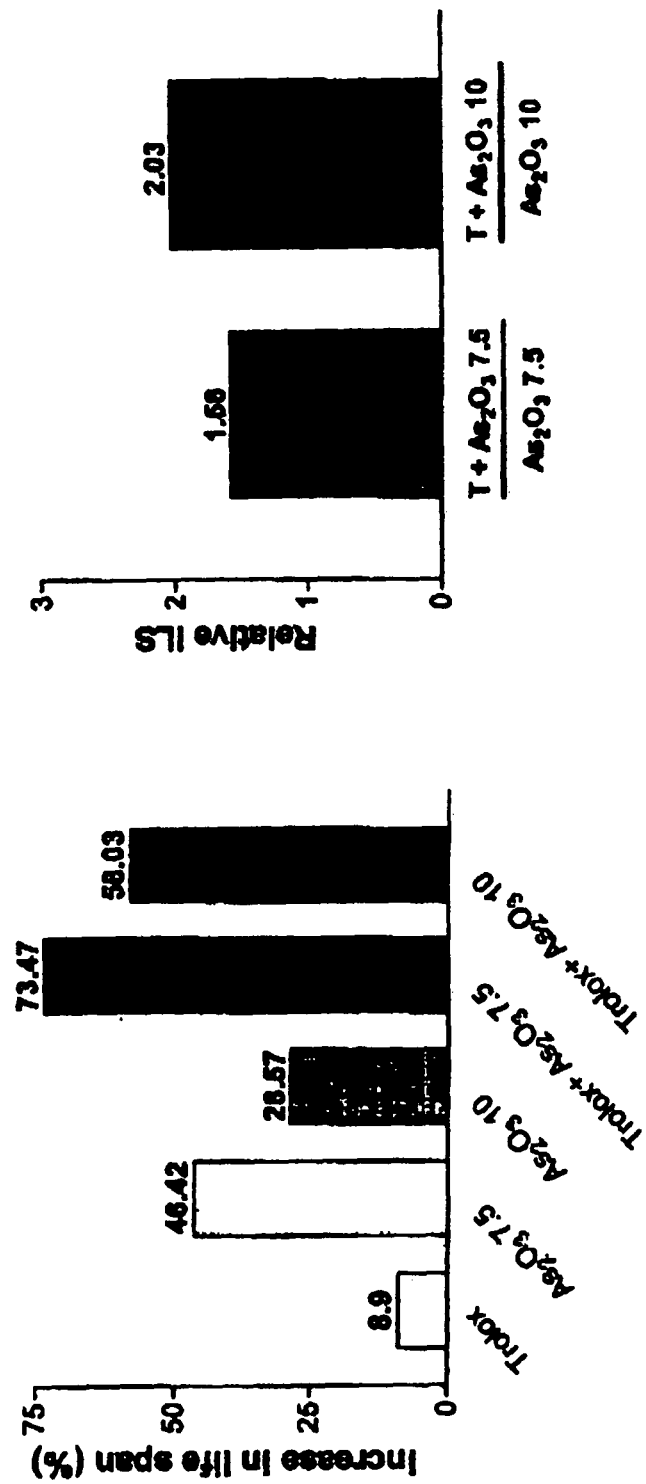

As shown in FIG. 12B the combination treatment improved survival time, with an increase in life span (ILS) of 46.4% when animals were treated with $As_2O_3$ 7.5 mg/kg. When the same dose was combined with trolox we observed an ILS of 73.5%. The significantly prolonged survival was without additive toxicity as compared with $As_2O_3$ or trolox treatment alone. The use of 10 mg/kg of $As_2O_3$ increased the life span of the treated mice only by 28.6%. Previous results suggested that this dose is toxic in BDF1 mice. However, the addition of trolox more than doubled the ILS at this dose of $As_2O_3$ (FIG. 12B).

EXAMPLE 3

Chronic myelogenous leukemia (CML) is a haematological malignancy that affects the myeloid lineage. In most cases of CML, the leukemic cells share a chromosome abnormality: a reciprocal translocation between one chromosome 9 and one chromosome 22 resulting in the fusion of two proteins Bcr and Abl. The selective Abl kinase inhibitor, STI-571 (a small molecule Abl inhibitor developed by Novartis), is toxic to CML cells in culture, causes regression of CML tumors in nude mice, and is currently used to treat CML patients.

In an attempt to analyze the efficacy of a combined theraphy using As2O3, Trolox and the new dual Src/Abl kinase inhibitor (SKI606), animal experiments were conducted as follows: CML cells (BaF stable transfected with mutated Bcr-Abl tyrosine kinase) were implanted subcutaneous in nude mice. After 24 hours, animals were divided in groups and injected intraperitoneally with saline solution, As2O3 (5 mg/kg), and Trolox 50 mg/kg alone or in combination. SKI (75 mg/kg) was injected intravenous in all the animals except controls. Animals were treated every day for 11 days. After 8 days the non-treated animals (Controls) developed tumors. In the animals treated with As2O3+SKI606 tumors were developed after 10 days and the group treated with As2O3+ Trolox+SKI606 was tumor free after 29 days, when the animals were sacrificed.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for treating a mammal suffering from a neoplastic disease, the method comprising administering to said mammal a pharmaceutically effective amount of a composition comprising arsenic trioxide and 5 to 50 mg/kg body weight of 6-hydroxy-2,5,7,8-tetramethylchroman-2-carboxylic acid wherein the 6-hydroxy-2,5,7,8-tetramethylchroman-2-carboxylic acid enhances inhibition by the arsenic trioxide of hyperproliferation of the neoplastic cells.

2. The method of claim 1, wherein said mammal is a human.

3. The method of claim 1, wherein said administering comprises intravenous, subcutaneous, intraperitoneal, intrathecal, intravesical, intradermal, intramuscular, or intralymphatic treatment.

4. The method of claim 1, wherein the 6-hydroxy-2,5,7,8-tetramethylchroman-2-carboxylic acid protects non-cancerous cells in the mammal from toxicity induced by the arsenic compound.

5. The method of claim 4, wherein the non-cancerous cells are liver cells.

6. The method of claim 1, wherein hyperproliferation of the neoplastic cells is inhibited.

7. The method of claim 1, wherein apoptosis is induced in the neoplastic cells.

8. The method of claim 1, wherein the 6-hydroxy-2,5,7,8-tetramethylchroman-2-carboxylic acid and arsenic trioxide act synergistically to inhibit hyperproliferation of the neoplastic cells.

9. The method of claim 1, wherein the 6-hydroxy-2,5,7,8-tetramethylchroman-2-carboxylic acid and the arsenic trioxide act synergistically to induce apoptosis and/or to induce oxidative stress in the neoplastic cells.

10. The method of claim 1, wherein the amount of 6-hydroxy-2,5,7,8-tetramethylchroman-2-carboxylic acid is about 50 mg/kg body weight.

11. A method for inducing apoptosis in neoplastic cells, said method comprising contacting said neoplastic cells with an effective amount of a composition comprising arsenic trioxide and 5 to 50 mg/kg body weight of 6-hydroxy-2,5,7,8-tetramethylchroman-2-carboxylic acid (Trolox™) that is non-toxic to neoplastic cells, wherein the Trolox™ enhances induction by the arsenic trioxide of the apoptosis.

12. The method of claim 11, wherein hyperproliferation of the neoplastic cells is inhibited.

13. The method of claim 11, wherein the 6-hydroxy-2,5,7,8-tetramethylchroman-2-carboxylic acid and the arsenic trioxide act synergistically to induce the apoptosis.

14. The method of claim 12, wherein the 6-hydroxy-2,5,7,8-tetramethylchroman-2-carboxylic acid and the arsenic trioxide act synergistically to inhibit the hyperproliferation of the neoplastic cells.

\* \* \* \* \*